US008262388B2

(12) United States Patent
Dunne et al.

(10) Patent No.: US 8,262,388 B2
(45) Date of Patent: Sep. 11, 2012

(54) LOCAL ENFORCEMENT OF ACCURACY IN FABRICATED MODELS

(75) Inventors: Patrick Colm Dunne, Maynard, MA (US); Eric B. Paley, Cambridge, MA (US); Micah J. Rosenbloom, Boston, MA (US); Michael Patrick Girard, Amherstburg (CA)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 12/710,721

(22) Filed: Feb. 23, 2010

(65) Prior Publication Data

US 2010/0152872 A1   Jun. 17, 2010

Related U.S. Application Data

(62) Division of application No. 11/467,866, filed on Aug. 28, 2006, now Pat. No. 7,698,014.

(60) Provisional application No. 60/761,078, filed on Jan. 20, 2006.

(51) Int. Cl.
*A61C 11/00* (2006.01)

(52) U.S. Cl. ........................................................ 433/60

(58) Field of Classification Search .............. 433/49–68, 433/34, 74
See application file for complete search history.

(56) References Cited

U.S. PATENT DOCUMENTS

| 4,103,424 A | 8/1978 | Benjamin et al. |
| 4,185,387 A | 1/1980 | Weber |
| 4,265,619 A * | 5/1981 | Lucki et al. ..................... 433/54 |
| 4,270,901 A | 6/1981 | Comparetto |
| 4,624,639 A * | 11/1986 | Wong ............................... 433/56 |
| 4,663,720 A | 5/1987 | Duret et al. |
| 4,837,732 A | 6/1989 | Brandestini et al. |
| 4,846,684 A | 7/1989 | Oestreich |
| 5,092,022 A | 3/1992 | Duret |
| 5,368,478 A | 11/1994 | Andreiko et al. |
| 5,372,502 A | 12/1994 | Massen et al. |
| 5,417,572 A | 5/1995 | Kawai et al. |
| 5,644,386 A | 7/1997 | Jenkins et al. |
| 5,658,143 A * | 8/1997 | Kuperman ....................... 433/60 |
| 5,740,222 A | 4/1998 | Fujita et al. |
| 5,740,802 A | 4/1998 | Nafis et al. |
| 5,768,134 A | 6/1998 | Swaelens et al. |
| 5,771,310 A | 6/1998 | Vannah |
| 5,999,840 A | 12/1999 | Grimson et al. |
| 6,019,601 A | 2/2000 | Cho |
| 6,044,232 A | 3/2000 | Pan |

(Continued)

FOREIGN PATENT DOCUMENTS

DE    10 2005 016 245 A1   10/2006

(Continued)

OTHER PUBLICATIONS

European Search Report, PCT/US2007/001547, May 11, 2010.

(Continued)

*Primary Examiner* — Cris L Rodriguez
*Assistant Examiner* — Hao D Mai

(57) ABSTRACT

The systems and methods disclosed herein employ a combination of digital three-dimensional modeling and rapid fabrication technologies to provide pre-indexed, pre-registered, and/or precut components for articulated dental models. Dental articulators and components of dental models as described herein use a positioning key to encode positional information for components of the dental model, and/or a reference grid on mounting surfaces to enforce local accuracy of fabricated parts against a fixed reference array.

13 Claims, 15 Drawing Sheets

U.S. PATENT DOCUMENTS

| | | | |
|---|---|---|---|
| 6,062,861 A | 5/2000 | Andersson | |
| 6,099,314 A | 8/2000 | Kopelman et al. | |
| 6,106,284 A * | 8/2000 | Cronin et al. | 433/34 |
| 6,141,105 A | 10/2000 | Yahashi et al. | |
| 6,201,541 B1 | 3/2001 | Shalom et al. | |
| 6,201,880 B1 | 3/2001 | Elbaum et al. | |
| 6,201,889 B1 | 3/2001 | Vannah | |
| 6,247,927 B1 | 6/2001 | Walter | |
| 6,257,887 B1 | 7/2001 | Heckerman et al. | |
| 6,334,853 B1 | 1/2002 | Kopelman et al. | |
| 6,342,917 B1 | 1/2002 | Amenta | |
| 6,364,660 B1 | 4/2002 | Durbin et al. | |
| 6,409,504 B1 | 6/2002 | Jones et al. | |
| 6,447,453 B1 | 9/2002 | Roundhill et al. | |
| 6,511,318 B2 * | 1/2003 | Kim | 433/74 |
| 6,512,838 B1 | 1/2003 | Rafii et al. | |
| 6,516,213 B1 | 2/2003 | Nevo | |
| 6,542,249 B1 | 4/2003 | Kofman et al. | |
| 6,545,637 B1 | 4/2003 | Krull et al. | |
| 6,575,751 B1 | 6/2003 | Lehmann et al. | |
| 6,616,444 B2 | 9/2003 | Andreiko et al. | |
| 6,621,491 B1 | 9/2003 | Baumrind et al. | |
| 6,648,640 B2 | 11/2003 | Rubbert et al. | |
| 6,671,539 B2 | 12/2003 | Gateno et al. | |
| 6,687,393 B1 | 2/2004 | Skinner, Jr. | |
| 6,691,764 B2 | 2/2004 | Embert et al. | |
| 6,701,006 B2 | 3/2004 | Moore et al. | |
| 6,726,478 B1 | 4/2004 | Isiderio et al. | |
| 6,738,063 B2 | 5/2004 | Shen et al. | |
| 6,738,727 B2 | 5/2004 | Chang | |
| 6,754,370 B1 | 6/2004 | Hall-Holt et al. | |
| 6,775,404 B1 | 8/2004 | Pagoulatos et al. | |
| 6,786,726 B2 | 9/2004 | Lehmann et al. | |
| 6,819,318 B1 | 11/2004 | Geng | |
| 6,821,123 B2 | 11/2004 | Andersson et al. | |
| 6,834,119 B2 | 12/2004 | Chen | |
| 6,856,321 B2 | 2/2005 | Tsukizaki et al. | |
| 6,882,894 B2 | 4/2005 | Durbin et al. | |
| 6,920,242 B1 | 7/2005 | Moore et al. | |
| 6,947,038 B1 | 9/2005 | Anh et al. | |
| 6,957,118 B2 | 10/2005 | Kopelman et al. | |
| 6,976,627 B1 | 12/2005 | Culp et al. | |
| 6,992,894 B1 | 1/2006 | Mease et al. | |
| 6,996,261 B2 | 2/2006 | deCharms | |
| 7,010,150 B1 | 3/2006 | Pfeiffer et al. | |
| 7,010,325 B1 | 3/2006 | Oh | |
| 7,020,325 B2 | 3/2006 | Park | |
| 7,061,485 B2 | 6/2006 | Tanguay, Jr. et al. | |
| 7,063,532 B1 | 6/2006 | Jones et al. | |
| 7,089,070 B1 | 8/2006 | Andersson et al. | |
| 7,103,212 B2 | 9/2006 | Hager et al. | |
| 7,112,065 B2 | 9/2006 | Kopelman et al. | |
| 7,118,375 B2 | 10/2006 | Durbin et al. | |
| 7,133,042 B2 | 11/2006 | Anh et al. | |
| 7,162,075 B2 | 1/2007 | Littlefield et al. | |
| 7,175,435 B2 | 2/2007 | Andersson et al. | |
| 7,194,112 B2 | 3/2007 | Chen et al. | |
| 7,220,124 B2 | 5/2007 | Taub et al. | |
| 7,245,743 B2 | 7/2007 | Littlefield et al. | |
| 7,280,682 B2 | 10/2007 | Littlefield et al. | |
| 7,286,954 B2 | 10/2007 | Kopelman et al. | |
| 7,292,716 B2 | 11/2007 | Kim | |
| 7,373,286 B2 | 5/2008 | Nikolskiy et al. | |
| 7,428,481 B2 | 9/2008 | Nikolskiy et al. | |
| 7,474,932 B2 | 1/2009 | Geng | |
| 7,476,100 B2 | 1/2009 | Kuo | |
| 7,523,044 B2 | 4/2009 | Rosenblood | |
| 7,545,372 B2 | 6/2009 | Kopelman et al. | |
| 7,581,953 B2 | 9/2009 | Lehmann et al. | |
| 7,605,817 B2 | 10/2009 | Zhang et al. | |
| 7,819,662 B2 | 10/2010 | Marshall et al. | |
| 2002/0009380 A1 | 1/2002 | Daskalon et al. | |
| 2002/0031743 A1 | 3/2002 | Kim | |
| 2002/0055800 A1 | 5/2002 | Nikolskiy et al. | |
| 2002/0102009 A1 | 8/2002 | Jones et al. | |
| 2002/0119432 A1 | 8/2002 | Ranta et al. | |
| 2002/0180760 A1 | 12/2002 | Rubbert et al. | |
| 2003/0003420 A1 | 1/2003 | Striezel | |
| 2004/0029078 A1 | 2/2004 | Marshall | |
| 2004/0133293 A1 | 7/2004 | Durbin et al. | |
| 2004/0155975 A1 | 8/2004 | Hart et al. | |
| 2004/0179728 A1 | 9/2004 | Littlefield et al. | |
| 2004/0197727 A1 | 10/2004 | Sachdeva et al. | |
| 2004/0204787 A1 | 10/2004 | Kopelman et al. | |
| 2004/0220691 A1 | 11/2004 | Hofmeister et al. | |
| 2005/0023710 A1 | 2/2005 | Brodkin et al. | |
| 2005/0070782 A1 | 3/2005 | Brodkin | |
| 2005/0089214 A1 | 4/2005 | Rubbert et al. | |
| 2005/0089822 A1 | 4/2005 | Geng | |
| 2005/0153255 A1 | 7/2005 | Sportbert et al. | |
| 2005/0153257 A1 | 7/2005 | Durbin et al. | |
| 2005/0170309 A1 | 8/2005 | Raby et al. | |
| 2005/0177261 A1 | 8/2005 | Durbin et al. | |
| 2005/0186540 A1 | 8/2005 | Taub et al. | |
| 2005/0250075 A1 | 11/2005 | Taub et al. | |
| 2006/0003292 A1 | 1/2006 | Lauren et al. | |
| 2006/0093988 A1 | 5/2006 | Swaelens et al. | |
| 2006/0127858 A1 * | 6/2006 | Wen | 433/213 |
| 2006/0154198 A1 | 7/2006 | Durbin et al. | |
| 2006/0172261 A1 | 8/2006 | Garry | |
| 2006/0263738 A1 | 11/2006 | Kuo | |
| 2007/0026363 A1 | 2/2007 | Lehmann et al. | |
| 2007/0172101 A1 | 7/2007 | Kriveshko et al. | |
| 2007/0172112 A1 | 7/2007 | Paley et al. | |
| 2008/0124681 A1 | 5/2008 | Cha | |
| 2008/0199829 A1 | 8/2008 | Paley et al. | |
| 2008/0233528 A1 | 9/2008 | Kim et al. | |

FOREIGN PATENT DOCUMENTS

| | | |
|---|---|---|
| EP | 0 837 659 B1 | 4/1998 |
| EP | 1 650 529 A1 | 4/2006 |
| WO | WO 00/08415 | 2/2000 |
| WO | WO 00/19929 | 4/2000 |
| WO | WO 2004/044787 A2 | 5/2004 |
| WO | WO 2004/100067 A2 | 11/2004 |

OTHER PUBLICATIONS

European Search Report, PCT/US2007/001652, May 11, 2010.
Koidis et al., "3D Visualization of Dental Data for Virtual Treatment Planning" 2004, 6 pages.
Xia, et al. "Three-Dimensional Virtual-Reality Surgical Planning and Soft-Tissue Prediction for Orthognathic Surgery" IEEE Transactions on Information Technology in Biomedicines, vol. 5, No. 2, Jun. 2001, pp. 97-107.
Ruzinkiewicz et al., "Real-Time 3D Model Acquisition" http://www.cs.princeton.edu/~smr/papers/rt_model (2002), 9 pages.
Williams et al., "A technique for fabricating patterns for removable partial denture frameworks using digitized casts and electronic surveying" The Journal of Prosthetic Dentistry, vol. 91, No. 1, Jan. 2994, pp. 85-88.
"Digital impressions: eliminating the weak link" Lab Management Today, Jan. 2006, 4 pages.
Incompetech "Free Online Graph Paper/Grid Paper PDFs", http://incompetech.com/graphpapger/trianglehex.html, printed Jul. 6, 2009, 3 pages.
International Search Report, PCT/US2007/001547, Jul. 2, 2007.
International Search Report, PCT/US2007/001652, Jun. 25, 2007.
International Search Report, PCT/US2007/001396, Jul. 23, 2007.

* cited by examiner

LOCAL ENFORCEMENT OF ACCURACY IN FABRICATED MODELS

RELATED APPLICATIONS

This application is a divisional of U.S. Ser. No. 11/467,866, filed Aug. 28, 2006 now U.S. Pat. No. 7,698,014, now allowed, which claims the benefit of U.S. Provisional Application No. 60/761,078, filed Jan. 20, 2006, the disclosure of which is incorporated by reference in their entirety herein.

BACKGROUND

The invention relates to dentistry, and more particularly to fabrication of dental objects and articulators.

Conventional dentistry employs physical casts of human dentition as a foundation for a variety of fabrication techniques. The impression materials used in this process, such as polymerizing silicone and polyether, theoretically capture an accurate dental impression. However, the initial impression may be flawed, and even a perfect impression may degrade over time as a result of thermal fluctuations, inherent plasticity, and rough handling. While the materials used to obtain dental impressions and create subsequent dental models have improved, the basic process steps remain prone to human error.

Sometimes, errors become so severe that the desired end product, such as a crown, cannot be manufactured. In other cases, the process introduces just enough error that the resulting prosthetic simply will not fit into a target space within a dental patient's dentition. This latter difficulty may place significant burdens on the craftsmanship of the practicing dentist to work the prosthetic and/or tooth surface into a suitable shape, or cause increased delay and costs if a new impression is required.

As another disadvantage, the process of taking the impression may cause significant discomfort to a patient, who must retain the impression material in the mouth while an impression is curing.

Recent advances in three dimensional imaging technology have introduced the possibility of a handheld, three-dimensional scanner that can be suitably adapted to acquisition of highly accurate, detailed surface data directly from within a dental patient's mouth—a virtual digital dental impression—that, once captured accurately, will not degrade, and can be easily reviewed, analyzed, and/or transmitted to remote manufacturing facilities.

While this technology introduces the possibility of significant advances in digital dentistry, there remains a need for improved dental processes and models that employ virtual digital dental impressions to reduce manual labor and opportunities for error inherent in conventional dentistry.

SUMMARY

The systems and methods disclosed herein employ a combination of digital three-dimensional modeling and rapid fabrication technologies to provide pre-indexed, pre-registered, and/or precut components for articulated dental models. Dental articulators and components of dental models as described herein use a positioning key to encode positional information for components of the dental model, and/or a reference grid on mounting surfaces to enforce local accuracy of fabricated parts against a fixed reference array.

BRIEF DESCRIPTION OF THE DRAWINGS

The invention and the following detailed description of certain embodiments thereof may be understood by reference to the following figures.

DETAILED DESCRIPTION

Figure 1:
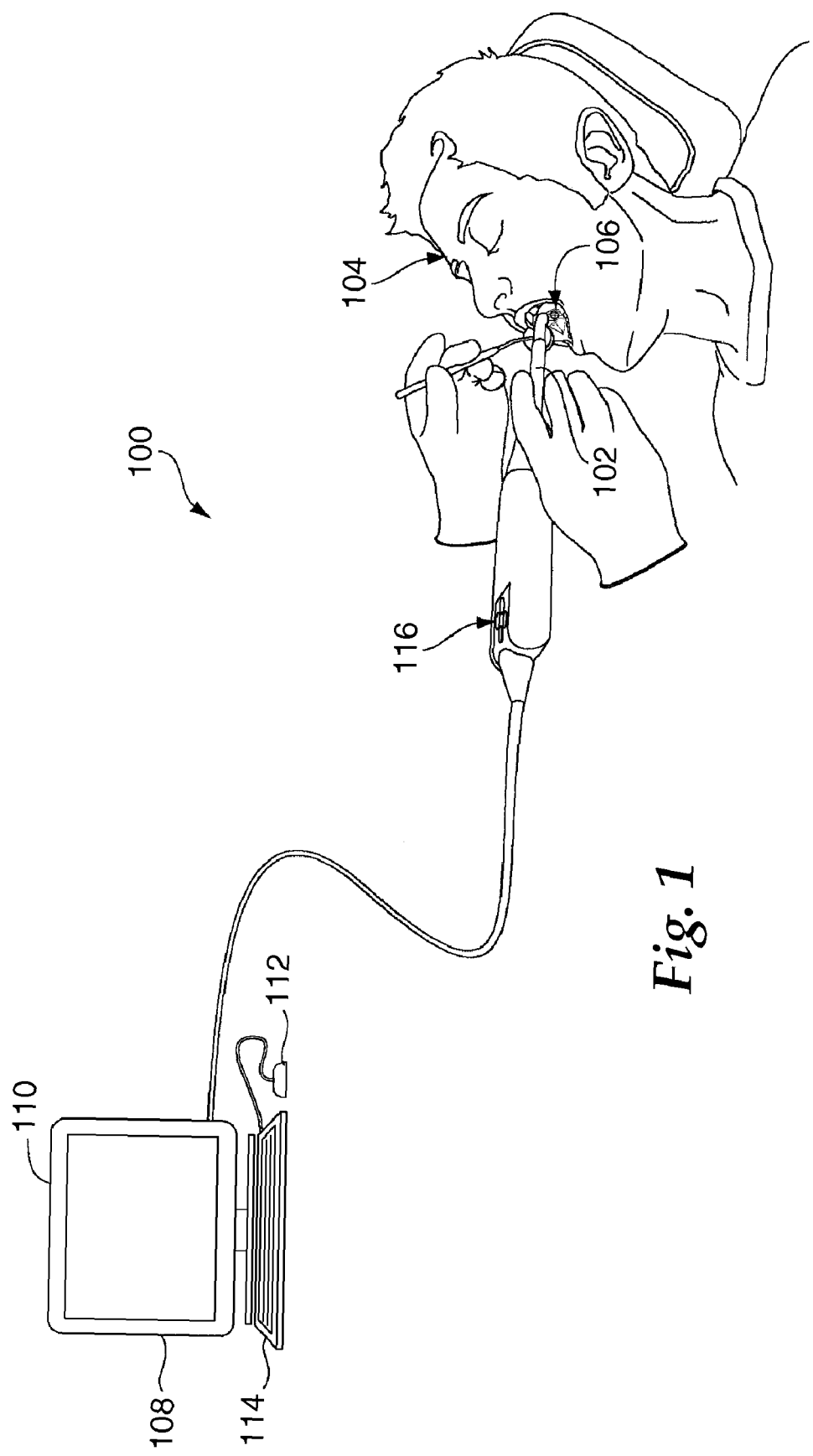
FIG. 1 shows a dental image capture system.

Described herein are systems and methods of fabricating dental objects for use in dental articulators based upon three-dimensional digital data captured from an intraoral scan. While the description emphasizes certain scanning technologies and certain combinations of fabrication techniques, it will be understood that additional variations, adaptations, and combinations of the methods and systems below will be apparent to one of ordinary skill in the art, such as fabrication of dental restorations not specifically described, or use of three-dimensional output or fabrication technologies not specifically identified herein, and all such variations, adaptations, and combinations are intended to fall within the scope of this disclosure. Further, while the techniques described herein are particularly useful for mechanical alignment of pieces of an articulating dental model, and manufacturing and design of same, it will be understood that the techniques described herein may be more generally applied to any environment where it is desired to capture the alignment and relative motion of a number of separately manufactured rigid bodies.

In the following description, the term "image" generally refers to a two-dimensional set of pixels forming a two-dimensional view of a subject within an image plane. The term "image set" generally refers to a set of related two dimensional images that might be resolved into three-dimensional data. The term "point cloud" generally refers to a three-dimensional set of points forming a three-dimensional view of the subject reconstructed from a number of two-dimensional views. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional surface representation", "digital surface representation", "three-dimensional surface map", and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context.

A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that three-dimensional rendering technologies exist, and may be usefully employed with the systems and methods disclosed herein. As such, rendering should be interpreted broadly unless a narrower meaning is explicitly provided or otherwise clear from the context.

The term "dental object", as used herein, is intended to refer broadly to subject matter specific to dentistry. This may include intraoral structures such as dentition, and more typically human dentition, such as individual teeth, quadrants, full arches, pairs of arches which may be separate or in occlusion of various types, soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

FIG. 1 shows an image capture system. In general, the system 100 may include a scanner 102 that captures images from a surface 106 of a subject 104, such as a dental patient, and forwards the images to a computer 108, which may include a display 110 and one or more user input devices such as a mouse 112 or a keyboard 114. The scanner 102 may also include an input or output device 116 such as a control input (e.g., button, touchpad, thumbwheel, etc.) or a display (e.g., LCD or LED display) to provide status information.

The scanner 102 may include any camera or camera system suitable for capturing images from which a three-dimensional point cloud may be recovered. For example, the scanner 102 may employ a multi-aperture system as disclosed, for example, in U.S. Pat. Pub. No. 20040155975 to Hart et al., the entire contents of which is incorporated herein by reference. While Hart discloses one multi-aperture system, it will be appreciated that any multi-aperture system suitable for reconstructing a three-dimensional point cloud from a number of two-dimensional images may similarly be employed. In one multi-aperture embodiment, the scanner 102 may include a plurality of apertures including a center aperture positioned along a center optical axis of a lens and any associated imaging hardware. The scanner 102 may also, or instead, include a stereoscopic, triscopic or other multi-camera or other configuration in which a number of cameras or optical paths are maintained in fixed relation to one another to obtain two-dimensional images of an object from a number of slightly different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging, or any other technology suitable for acquiring three-dimensional data, or two-dimensional data that can be resolved into three-dimensional data.

In one embodiment, the scanner 102 is a handheld, freely positionable probe having at least one user input device 116, such as a button, lever, dial, thumb wheel, switch, or the like, for user control of the image capture system 100 such as starting and stopping scans. In an embodiment, the scanner 102 may be shaped and sized for dental scanning More particularly, the scanner may be shaped and sized for intraoral scanning and data capture, such as by insertion into a mouth of an imaging subject and passing over an intraoral surface 106 at a suitable distance to acquire surface data from teeth, gums, and so forth. The scanner 102 may, through such a continuous acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthetic, to ensure proper fitting using a previous scan of corresponding dentition, such as a tooth surface prepared for the prosthetic.

Although not shown in FIG. 1, it will be appreciated that a number of supplemental lighting systems may be usefully employed during image capture. For example, environmental illumination may be enhanced with one or more spotlights illuminating the subject 104 to speed image acquisition and improve depth of field (or spatial resolution depth). The scanner 102 may also, or instead, include a strobe, flash, or other light source to supplement illumination of the subject 104 during image acquisition.

The subject 104 may be any object, collection of objects, portion of an object, or other subject matter. More particularly with respect to the dental fabrication techniques discussed herein, the object 104 may include human dentition captured intraorally from a dental patient's mouth. A scan may capture a three-dimensional representation of some or all of the dentition according to particular purpose of the scan. Thus the scan may capture a digital model of a tooth, a quadrant of teeth, or a full collection of teeth including two opposing arches, as well as soft tissue or any other relevant intraoral structures. In other embodiments where, for example, a completed fabrication is being virtually test fit to a surface preparation, the scan may include a dental prosthesis such as an inlay, a crown, or any other dental prosthesis, dental hardware, dental appliance, or the like. The subject 104 may also, or instead, include a dental model, such as a plaster cast, wax-up, impression, or negative impression of a tooth, teeth, soft tissue, or some combination of these.

The computer 108 may be, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the subject 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom.

In an example of general operation of a three-dimensional image capture system 100, the scanner 102 may acquire two-dimensional image sets at a video rate while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system employs camera motion estimation to avoid the need for independent tracking of the position of the scanner 102. One useful example of such a technique is described in commonly-owned U.S. application Ser. No. 11/270,135, filed on Nov. 9, 2005, the entire contents of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In some embodiments, the display may include a touch screen interface using, for example capacitive, resistive, or surface acoustic wave (also referred to as dispersive signal) touch screen technologies, or any other suitable technology for sensing physical interaction with the display 110.

Figure 2:
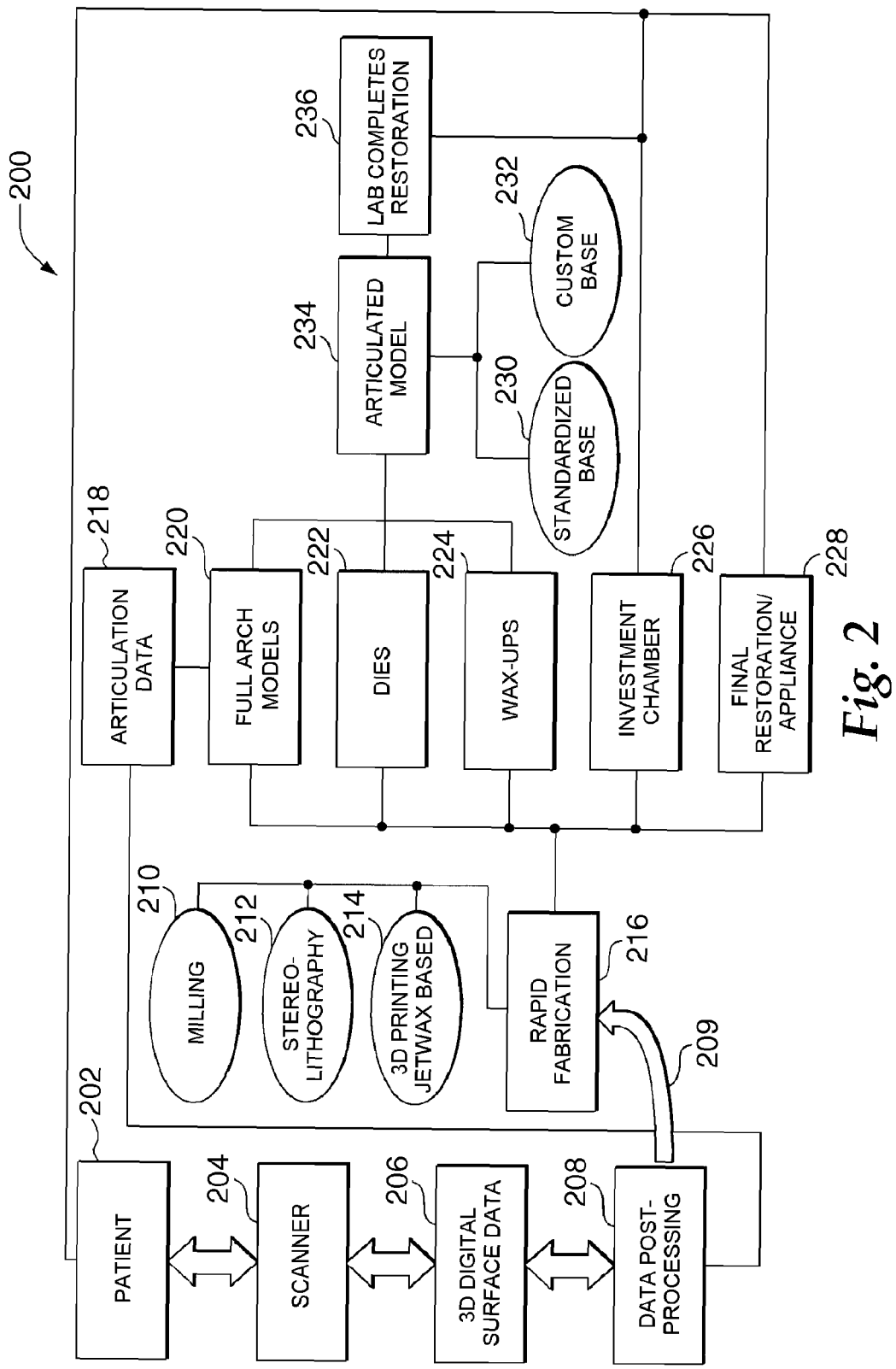
FIG. 2 is a block diagram of a generalized manufacturing process for dental objects.

FIG. 2 is a conceptual block diagram of participants in a generalized manufacturing process for dental objects. The system 200 may begin with a patient 202 being scanned by a scanner 204, such as the scanner 102 and image capture system 100 described above, to obtain a digital surface representation 206 of one or more intraoral structures. This may include scans before and/or after a surface has been prepared to receive a dental restoration or other dental object. So, for example, a pre-preparation scan may be taken to capture a shape of the original anatomy and any occlusion information useful in creating a restoration, and a prepared surface scan may be taken to use as a basis for creating the restoration, and in particular for shaping the restoration to the prepared surface. Articulation data relating to the orientation and/or relative motion of an upper and lower arch may also be obtained through one or more scans of the arches in occlusion, or through other techniques such as still images or video of the arches in various orientations, or various dimensional measurements captured directly from the arches, or a physical bite registration captured on a thin sheet of material.

In one embodiment, a second scanner such as a PMD [vision] camera from PMD Technologies, may be employed to capture real-time, three-dimensional data on dynamic articulation and occlusion. While this scanner employs different imaging technology (time-of-flight detection from an array of LEDs) than described above, and produces results with resolution generally unsuitable for reconstruction of dental models, such a scanner may be employed to infer motion of, e.g., opposing dental arches with sufficient resolution to select an axis for articulation or otherwise capture dynamic information that can be applied to two or more rigid bodies of a dental object scan. This data may be supplemented with more precise alignment data statically captured from digital or manual bite registration to provide reference or calibration points for continuous, dynamic motion data.

The digital surface representation 206 may be processed with one or more post-processing steps 208. This may include a variety of data enhancement processes, quality control processes, visual inspection, and so forth. Post-processing steps may be performed at a remote post-processing center or other computer facility capable of post-processing the imaging file, which may be, for example a dental laboratory. In some cases, this post-processing may be performed by the image capture system 100 itself Post-processing may involve any number of clean-up steps, including the filling of holes, removing of outliers, etc.

Data enhancement may include, for example, smoothing, truncation, extrapolation, interpolation, and any other suitable processes for improving the quality of the digital surface representation 206 or improving its suitability for an intended purpose. In addition, spatial resolution may be enhanced using various post-processing techniques. Other enhancements may include modifications to the data, such as forming the digital surface representation 206 into a closed surface by virtually providing a base for each arch, or otherwise preparing the digital surface representation for subsequent fabrication steps.

In a quality control process, the digital surface representation 206 may be analyzed for the presence of holes or regions of incomplete or inadequate scan data. The digital surface representation 206 may also be automatically examined for unexpected curvature or asymmetry to a scanned arch, or other apparent defects in the acquired data. Other quality control processes may incorporate additional data. For example, a current scan may be compared to previous scans for the same patient. As another example, a selection of a dental restoration may be analyzed along with a scan of a tooth surface prepared for the restoration in order to evaluate the suitability of the surface preparation and any surrounding dentition for receiving the restoration. More generally, any process for evaluating data in the digital surface representation 206 with respect to its quality, internal consistency, or intended use, may be used in a post-processing quality control process.

The digital surface representation 206 may also be displayed for human inspection, such as by providing a perspective rendering of a point cloud of acquired surface data on a display.

Following any manual or automated post-processing, the resulting digital model may be transmitted to a rapid fabrication facility 216, as indicated by an arrow 209. In addition, articulation data 218 in any suitable form may be transmitted for use in subsequent processing steps, as well as a prescription or other specification for manufacture of a restoration, appliance, hardware, and the like. The rapid fabrication facility 216 may be a dental laboratory, an in-house dental laboratory at a dentist's office, or any other facility with machinery to fabricate physical models from digital models. The rapid fabrication facility 216 may, for example, include a milling system 210, a stereo lithography system 212, Digital Light Processing (not shown), or a three-dimensional printer 214, or some combination of these. The milling system 210 may include, for example, a CNC milling machine. Milling systems may be used to take a block of material and create a variety of outputs, including full-arch models, dies, wax-ups, investment chambers or a final restoration or appliance. Such blocks may include ceramic-based, particle-board, wax, metals or a variety of other materials. Dental milling systems such as Procera from Nobel Biocare Inc. or Cerec from Sirona Inc. may also be used to create a final dental hardware component. The stereo lithography system 212 may include, for example, a Viper System by 3D Systems, Inc. The three-dimensional printer 214 may include, for example, an InVision HR printer from 3D Systems. Each of these fabrication techniques will be described in greater detail below. Other techniques for three-dimensional manufacturing are known, such as Fused Deposition Modeling, Laminated Object Manufacturing, Selective Laser Sintering, and Ballistic Particle Manufacturing, and may be suitably be adapted to use in certain dental applications described herein. More generally, three-dimensional fabrication techniques continue to become available. All such techniques may be adapted to use with the systems and methods described herein, provided they offer suitable fabrication resolution in suitable materials for use with the various dental objects described herein.

The rapid fabrication facility 216 may use the articulation data 218 and the digital model to generate one or more dental objects, such as one or more full arch models 220, one or more dies 222, one or more waxups 224, one or more investment chambers 226, and/or one or more final restorations or appliances 228. Some components, such as the dies 222 and arches 220, may be inserted into an articulated model 234 such as an articulator with a standard base 230 or a custom base 232. Articulators and articulated models are described in greater detail below. A dental laboratory may employ these various components to complete a restoration 236, which may be returned to a dentist for placement into/onto the dentition of the dental patient.

Various aspects of this system and process will now be described in greater detail, beginning with the rapid fabrication techniques that may be employed with the systems and methods described herein.

Figure 3:
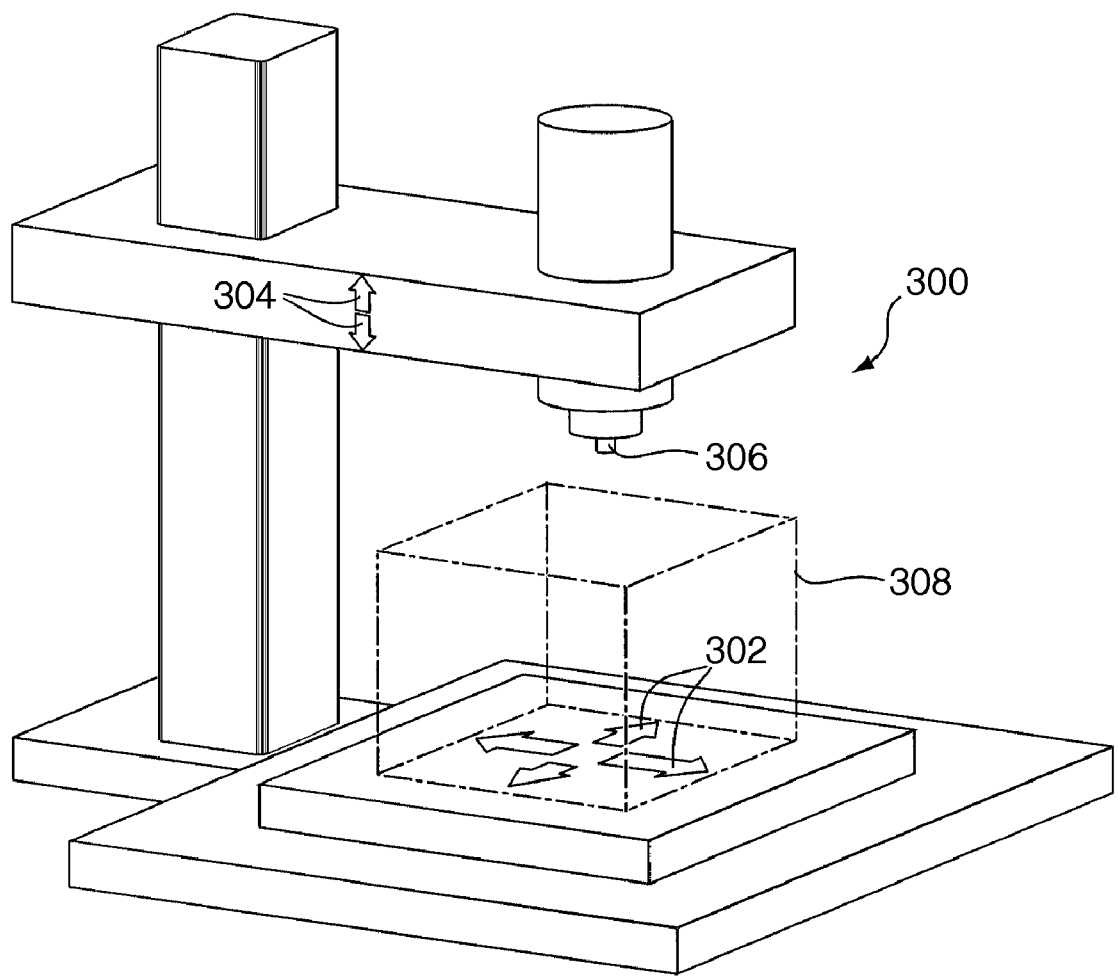
FIG. 3 shows a milling machine.

FIG. 3 shows a milling machine that may be used with the systems and methods herein. In particular, FIG. 3 illustrates a Computerized Numerically Controlled ("CNC") milling machine 300 including a table 302, an arm 304, and a cutting tool 306 that cooperate to mill under computer control within a working envelope 308. In operation, a workpiece (not shown) may be attached to the table 302. The table 302 may move within a horizontal plane and the arm 304 may move on a vertical axis to collectively provide x-axis, y-axis, and z-axis positioning of the cutting tool 306 relative to a workpiece within the working envelope 308. The cutting tool 306 may thus be maneuvered to cut a computer-specified shape from the workpiece.

Milling is generally a subtractive technology in that material is subtracted from a block rather than added. Thus pre-cut workpieces approximating commonly milled shapes may advantageously be employed to reduce the amount of material that must be removed during a milling job, which may reduce material costs and/or save time in a milling process. More specifically in a dental context, it may be advantageous to begin a milling process with a precut piece, such as a generic coping, rather than a square block. A number of sizes and shapes (e.g., molar, incisor, etc.) of preformed workpieces may be provided so that an optimal piece may be selected to begin any milling job. Various milling systems have different degrees of freedom, referred to as axes. Typically, the more axes available (such as 4-axis milling), the more accurate the resulting parts. High-speed milling systems are commercially available, and can provide high throughputs.

In addition a milling system may use a variety of cutting tools, and the milling system may include an automated tool changing capability to cut a single part with a variety of cutting tools. In milling a dental model, accuracy may be adjusted for different parts of the model. For example, the tops of teeth, or occlusal surfaces, may be cut more quickly and roughly with a ball mill and the prepared tooth and dental margin may be milled with a tool resulting in greater detail and accuracy. In general, milling systems offer the advantage of working directly with a finished material so that the final product is free from curing-related distortions or other artifacts. As a disadvantage, a high precision requires smaller cutting tools and correspondingly slower fabrication times.

CNC milling and other milling technologies can be employed for manufacturing dental models, dental model components, wax-ups, investment chambers, and other dental objects, some of which are described in greater detail below. In addition specialty dental milling equipment exists, such as the Cerac system from Sirona Dental. Another useful milling system for the dental fabrication processes described herein is a copy milling system that permits manual or automated transfer of a three-dimensional form from a physical object to a milled target.

All such milling systems as may be adapted to use in the dental applications described herein are intended to fall within the scope of the term "milling system" as used herein, and a milling process may employ any of the milling systems described herein.

Figure 4:
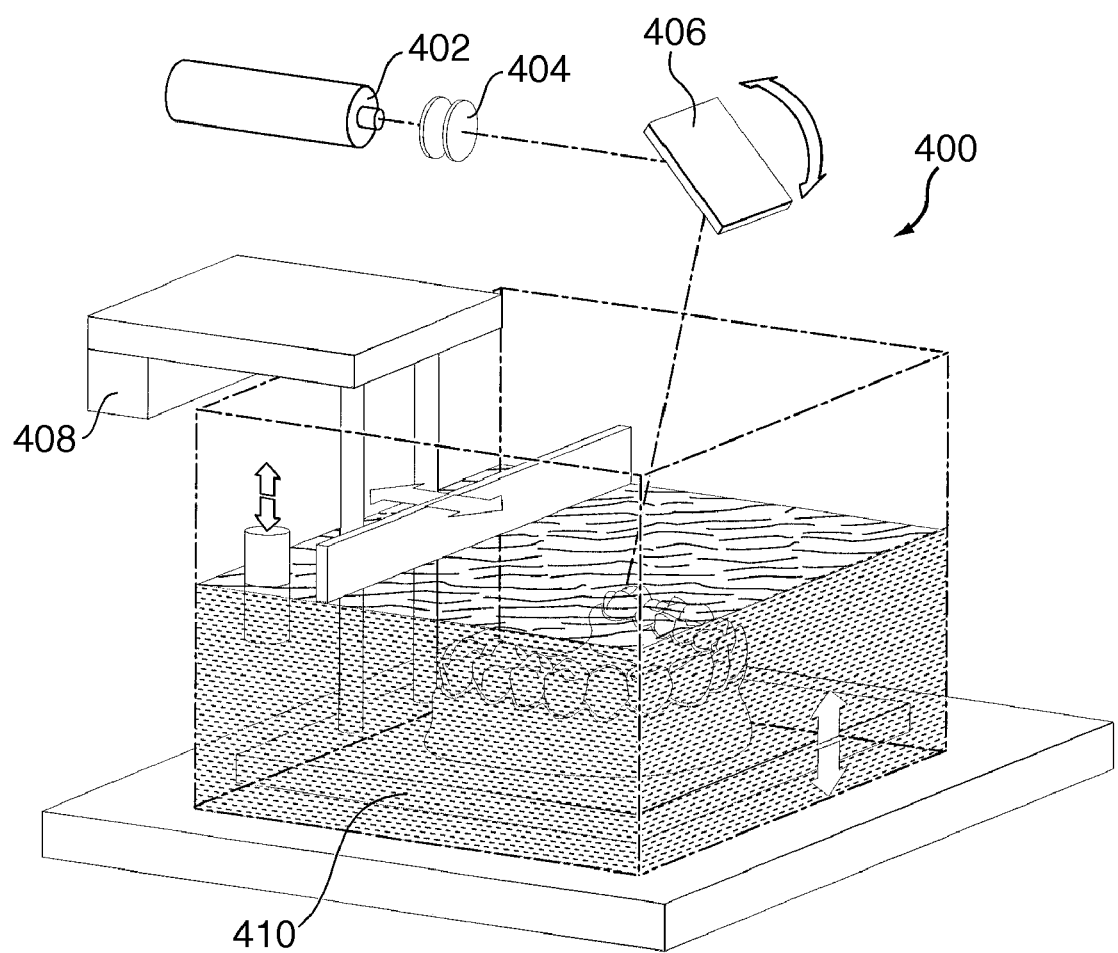
FIG. 4 shows a stereo lithography apparatus.

FIG. 4 shows a stereo lithography apparatus ("SLA") that may be used with the systems and methods described herein. In general, the SLA 400 may include a laser 402, optics 404, a steering lens 406, an elevator 408, a platform 410, and a straight edge 412, within a vat 412 filled with a polymer. In operation, the laser 402 is steered across a surface of the polymer to cure a cross-section of the polymer, typically a photocurable liquid resin, after which the elevator 408 slightly lowers the platform 408 and another cross section is cured. The straight edge 412 may sweep the surface of the cured polymer between layers to smooth and normalize the surface prior to addition of a new layer. In other embodiments, the vat 412 may be slowly filled with liquid resin while an object is drawn, layer by layer, onto the top surface of the polymer. One useful commercial embodiment of an SLA is the SCS-1000HD available from Sony Corporation.

Stereo lithography is well-suited for the high volume production of dental models and dies, because parts may be batched on machines for rapid production. When optimized, these parts may be used in lieu of plaster dental models and other dental objects. An SLA may be usefully employed for fabrication of dental models, arches and cast-able parts, as well as for other high-accuracy and/or high-throughput applications. In some embodiments an SLA may receive a digital surface representation directly from a clinician's intraoral scan, and manufacture a dental model corresponding to the patient's dentition with or without surrounding soft tissue. Where groups of related objects are manufactured, they may be physically interconnected during the SLA process so that a complete set or kit is readily handled after fabrication. Individual pieces of the kit may be separated and trimmed or finished as appropriate, such as by a qualified technician in a dental laboratory. In such embodiments, dental objects may be oriented so that the interconnecting frame or other mechanical infrastructure only contacts objects on non-critical surfaces. Thus, for example, connections might be avoided on opposing surfaces of a dental arch where fine detail is to be preserved.

An SLA may require significant optimization of operating parameters such as draw speeds, beam diameters, materials, etc. These parameters may be stored in a "style" file, which may also vary accuracy and speed in different areas of a model. So, for example, a tooth within an arch that contains a surface prepared for a dental prosthetic may be optimized for detail/accuracy, while a distant tooth on a different arch may be optimized for speed.

A related technology, Digital Light Processing ("DLP"), also employs a container of curable polymer. However, in a DLP system, a two-dimensional cross section is projected onto the curable material to cure an entire transverse plane at one time. DLP fabrication currently provides resolution on the order of 40 microns, with further sub-pixel accuracy available using a number of techniques.

Figure 5:
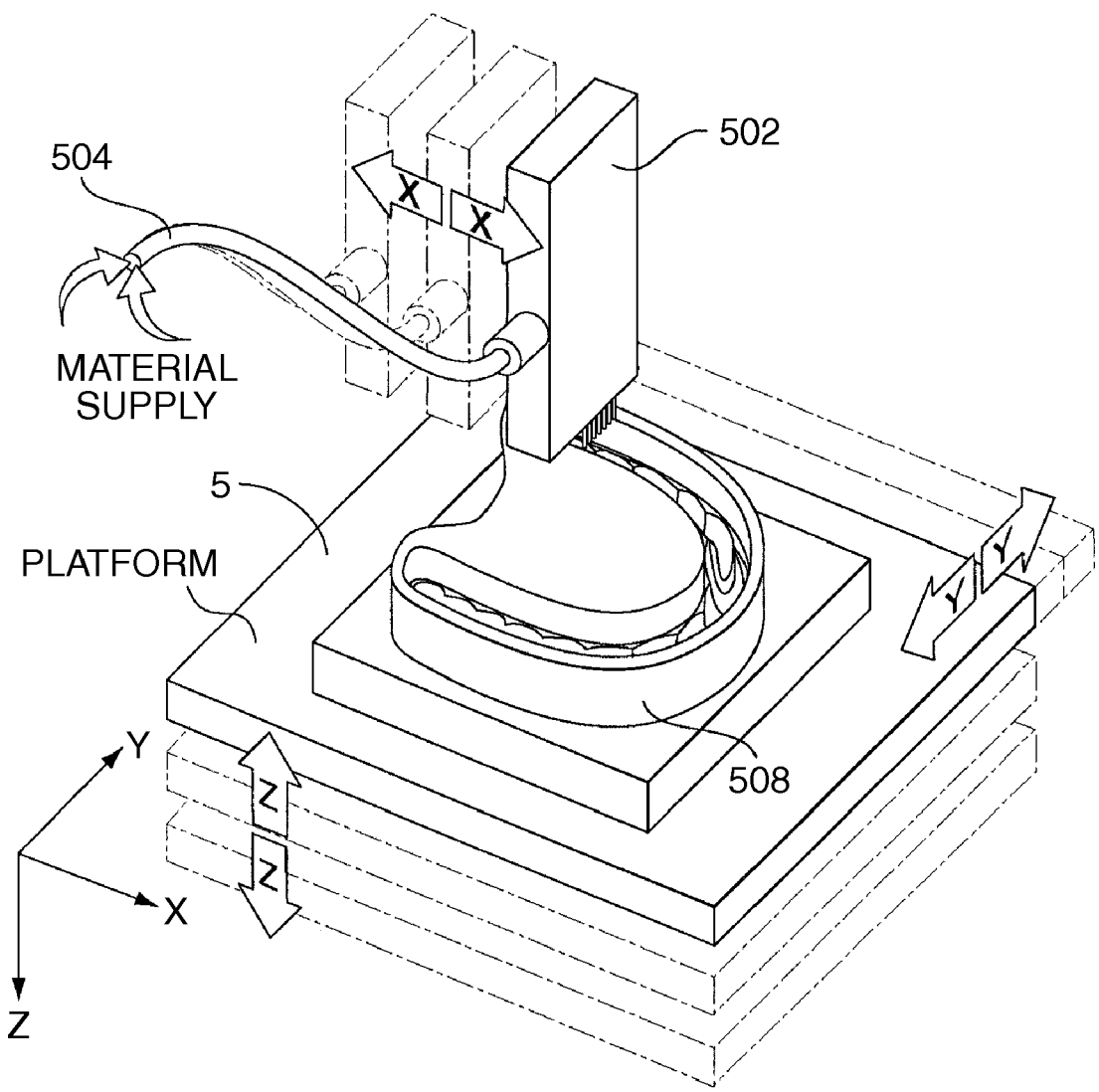
FIG. 5 shows a three-dimensional printer.

FIG. 5 shows a three-dimensional printer. The three-dimensional printer 500 may include a print head 502, a material supply 504, a platform 506, and positioning mechanisms (not shown) such as elevators, arms, belts, and the like that may be used to position the print head 502 relative to a printed item 508 during a printing operation. In operation, the print head 502 may deposit curable photopolymers or powders in a layer-by-layer fashion.

Various types of three-dimensional printers exist. Some printers deposit a polymer in conjunction with a support material or a bonding agent. In some systems, the stage may move as well to control x-y motion of the print head 502 relative to the platform 506 and printed item 508. Models printed on such systems may require finishing steps, such as removal of wax supports and other cleaning processes. Three-dimensional printers are well suited to rapid fabrication of small parts such as wax patterns or wax-ups, as well as dies and other relatively small dental objects. One commercial system suitable for three-dimensional dental printing applications is the InVision HR printer from 3D Systems.

Three-dimensional printing may be usefully employed for fabricating a variety of dental objects including wax-ups that may be cast by a dental laboratory to create a traditional metal substructure restoration, often referred to as a Porcelain-Fused-to-Metal ("PFM") restoration. Direct three-dimensional printing of the wax-up (much of the shape of which may be directly inferred from a digital surface representation of a patient's dentition) may omit intermediate processing steps in conventional dentistry, where the shape of the dentition travels from an impression to a model to a wax-up. This approach advantageously prevents loss or corruption of data between the source (the patient's dentition) and the target wax-up by transitioning directly from an intraoral scan to a waxup, bypassing intermediate processing steps. Other useful applications of three-dimensional printing are described below in greater detail.

It will be appreciated that other rapid prototyping systems are known in the art. Thus, the terms fabricate, fabricating, and fabrication, as used herein, will be understood to refer to the fabrication technologies above, as well as any other rapid prototyping or other manufacturing technology that might be adapted to manufacture of custom dental objects, including, without limitation, selective laser sintering ("SLS"), fused deposition modeling ("FDM"), laminated object manufacturing ("LOM"), and so forth, unless a different meaning is explicitly provided or otherwise clear from the context. Similarly, any of the above technologies, either alone or in combination, may operate as a means for fabricating, printing, manufacturing, or otherwise creating the dental objects described herein. It will be appreciated that the fabrication steps described above with reference to particular technologies may be followed by additional steps such as curing, cleaning, and so forth to provide a final product.

The manufacturing techniques described above may be combined in various ways to provide a multimodal fabrication process. Thus, for example, a CNC milling machine may be used to create a die for a tooth requiring greater detail than an SLA can provide, while the SLA may be employed for a model of a dental arch that contains the die. This multimodal approach may deploy the advantages of various technologies in different aspects of the fabrication process, such as using stereo lithography for speed, milling for accuracy, and three-dimensional printing for high-speed fabrication of small parts. In addition, as described in one of the examples below, other mass production techniques such as injection molding may be employed for certain standardized parts, such as an articulator.

Figure 6:
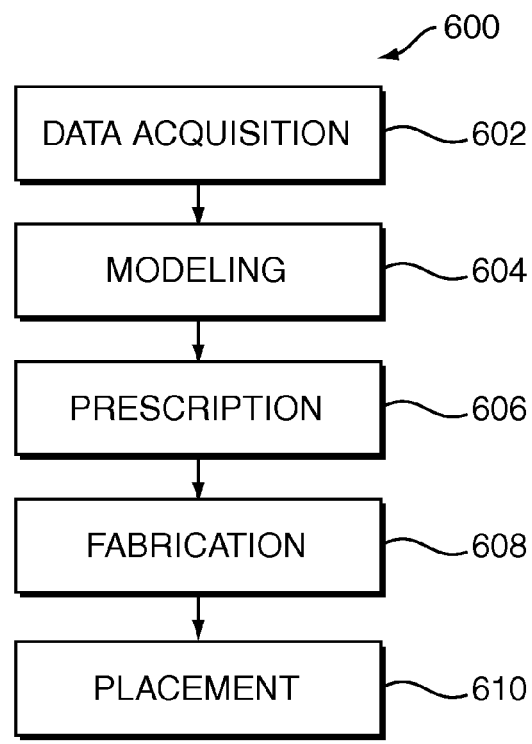
FIG. 6 is a high-level flow chart of a dental object fabrication process.

FIG. 6 is a high-level flow chart of a dental object fabrication process. This process 600 employs a three-dimensional representation of dentition acquired directly from an intraoral scan, and advantageously bypasses a number of processing steps used in conventional dentistry.

In general the process 600 may begin with data acquisition, as shown in step 602. Data acquisition may include any acquisition of a digital surface representation, or other three-dimensional or other representation of dentition suitable for use in a dental object fabrication process. The data acquisition may be performed using, for example, the scanner 102 and image capture system described above with reference to FIG. 1. In certain embodiments, a number of different scans may be acquired, such as scans to establish articulation and occlusion of arches, or scans before and after a surface preparation, which may be used jointly to create a prosthetic or the like. For example, to establish articulation and occlusion of arches, scans may be made of the upper and lower arches, and a bite scan may be taken with the upper and lower arches in various types of occlusion and so forth. Used jointly, these scans may provide full detail for an upper and lower arch, along with static and dynamic data concerning the alignment and motion of the arches.

Once suitable data has been acquired, one or more modeling operations may be performed, as shown in step 604. This may include modeling steps such as ditching a virtual die of a digital dental model, specifying a tooth for treatment, filling holes or otherwise correcting data, bite registration, and/or fully designing a restoration, prosthetic, hardware or other dental object(s), as well as any other modeling or digital model manipulation useful in a dental context. Modeling may be performed using commercially available Computer Automated Design ("CAD") or other three-dimensional modeling tools, or special-purpose dental modeling software such as the inLab CAD/CAM system from Sirona.

For example, modeling may include bounding the surface representation to form a solid, and then creating a void space, or collection of void spaces within the solid that do not affect dentally significant surfaces such as the dentition or surrounding soft tissue. This may advantageously result in significant reductions in material required to fabricate a dental model from the voided digital model, thus reducing material costs as well as time to manufacture dental models.

Modeling for articulated models may include using scan data together with bite registration and other data to position two rigid bodies corresponding to opposing arches in a relative orientation corresponding to the position of the arches in a dental patient's mouth. Once so aligned, the arches may be mechanically registered to a common reference surface that corresponds to, e.g., the top and bottom of a dental articulator. This process is described in greater detail below.

As another example, modeling may include the computer aided design of an item of removable dental hardware. This may account for the shape of teeth and soft tissue, jaw position, occlusal and/or articulating relationships, soft palette and any other spatial or dynamic characteristics of a patient's mouth, as well as any objectives for the hardware. For example, a bruxism night guard may simply serve to separate opposing arches slightly, and may be designed to permit or prohibit breathing through the mouth. A suitable device may be virtually designed that fits the teeth, provides a small amount of intervening material, and conforms to any other aspects of the patient's mouth such as the tongue, lips, and the like. As another example, a snore night guard may be virtually designed to displace one arch slightly in a manner that provides greater clearance for the palette. Other items of removable hardware, such as a surgical guide, removable denture, or stent may similarly be virtually designed within a digital modeling environment. Once a design has been established, the resulting digital model may be fabricated using any of the fabrication techniques described below. A number of other modeling steps are described with reference to specific fabrication processes below. It will be appreciated that the term "modeling" as used herein may refer to any processing of a digital dental model including fully automated, semi-automated, and/or manual processes such as those noted throughout this description.

As shown in step 606, a prescription may be prepared. This specifies a type of restoration, prosthetic, or the like, and may include a variety of additional information related to a manufacturer, color, finish, die spacing, and so forth. It will be appreciated that the prescription step 606 may be performed before the modeling step 608, such as in a process where a dentist transmits the initial digital surface representation from a patient to a dental laboratory along with a prescription, leaving some or all of the modeling to the dental laboratory.

As shown in step 608, one or more dental objects may be fabricated. Fabrication may be performed using any of the fabrication technologies described above, either alone or in various combinations, using data from one of the modeling systems described above, which may be reformatted or otherwise adapted as necessary for a particular printing, milling, or other fabrication technology. Also, as will be clear from some of the examples below, fabrication may include a combination of different fabrication technologies. For example, dental model may be three-dimensionally printed with a space for a die, and the die may be milled of a different material for use in subsequent processing steps. Thus, the term "fabrication" as used herein is intended to refer to any suitable fabrication technology unless a specific fabrication technology is explicitly identified, or otherwise clear from the context. A number of specific fabrication examples are discussed below in greater detail.

As shown in step 610, a prosthetic or other dental object may be returned to a dentist for placement into a patient's dentition.

It will be appreciated that the above processes may be realized in hardware, software, or any combination of these suitable for the data acquisition and fabrication technologies described herein. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer and/or fabrication facility in a number of ways or all of the functionality may be integrated into a dedicated, standalone device. All such permutations and combinations are intended to fall within the scope of the present disclosure.

It will also be appreciated that means for performing the steps associated with the processes described above may include any suitable components of the image capture system 100 described above with reference to FIG. 1, as well as any components of the fabrication facilities described with reference to FIGS. 3-5, along with any software and/or hardware suitable for controlling operation of same. All such realizations and means for performing the processes disclosed herein are intended to fall within the scope of this disclosure.

Figure 7:
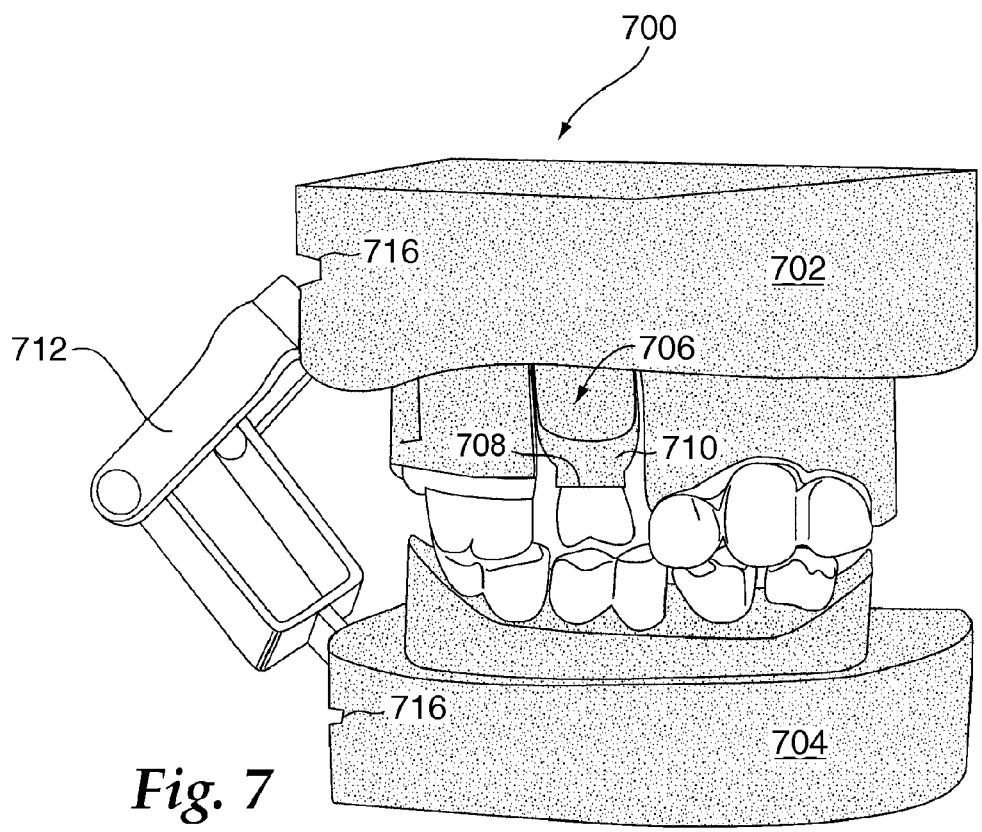
FIG. 7 illustrates a number of dental objects that can be fabricated from a three-dimensional representation of dentition.

FIG. 7 illustrates a number of dental objects that can be fabricated from a three-dimensional representation of dentition. A full arch model 700 may include an upper arch 702, a lower arch 704, a die 706 with a prepare surface 708 and a ditched region 710, and an articulator 712 that maintains the upper arch 702 and the lower arch 704 in a desired occlusal relationship. It will be appreciated that, while FIG. 7 depicts a single die 706 in the upper arch 702, a dental model 700 may include any number of dies 706, some or all of which may be in the lower arch 704.

Generally, the die 706 is manually cut from a dental model by a dental technician for preparation of a restoration or the like from the prepared surface 708 thereof. However, applying the principles described herein, the die may be virtually cut during the modeling step above, and separately fabricated using any of the techniques above. Thus in one embodiment, a technique for fabricating pre-cut dental models is disclosed. As a significant advantage, this approach removes a manual processing step from conventional dentistry. While the arches 702, 704 may, in general be fabricated using a process selected for high speed or low cost, the die may be fabricated using a process selected for hardness, or more generally, for suitability for subsequent processing steps. Thus in one embodiment the arches 702, 704 of the model may be fabricating using three-dimensional printing or DLP and the pre-cut die 706 may be fabricated using computerized milling. The die 706 may also, or instead, be pre-indexed using, e.g., a pair of posts on the die 706 and matching holes on the upper arch 702, so that, although manufactured separately, the die 706 may be mechanically registered to the upper arch 702.

In conventional dental fabrication, a die spacer (not shown) such as a thin painted film is often used to provide spacing between a model surface preparation and a dental component such as a crown or other restoration. The spacing may accommodate cement used to attach the final restoration to the actual surface preparation in a patient's mouth. The spacing may also account for dimensional changes that occur to various materials during drying, curing, or other handling during various fabrication steps and may provide a margin of error for a final restoration. In one aspect, a restoration may be virtually modeled directly from a digital surface representation of dentition before and after a surface preparation, which may advantageously remove the need for manually applied die spacers. In some embodiments where control of die spacer thickness is desired, or various types of intermediate physical modeling are anticipated, a die spacer may be virtually created and integrated into a model. The die spacer may be integrated directly into a printed component such as a die to account for any physical displacement or offset that the die spacer would have provided. In addition to virtual integration of dies spacers for a cementation voids or dimensional variation, the modeling step may include the addition of a layer of occlusal relief to provide similar accommodation for occlusal spacing between a restoration and a prepared surface (and by extension, between the restoration and a tooth of an opposing arch).

In various processes, it may be faster and/or cheaper to fabricate components of a dental model in a hollow form, that is, omitting any material not required for creating a prosthetic or fitting the prosthetic within occlusal surfaces of the arches 702, 704. Thus, portions of the upper arch 702, the lower arch 704, and/or the die 706 may be hollowed during the modeling step(s) in preparation for fabrication. Other modeling steps may usefully be performed. For example, it is common practice to "ditch" the die(s) of a dental model for increased physical exposure of the surface preparation, and in particular, the margin, for subsequent inspection, manipulation, and processing. This may be performed virtually such as through a modeling tool that permits automatic, semi-automatic, or manual ditching of a die in a digital surface representation or other digital model of dentition. In general, the degree of automation will depend on the ability to either automatically detect or provide by way of electronic annotation, a demarcation of the margin line for a surface preparation below which the die may be ditched.

Modeling may provide additional useful features to the dental model 700. For example, if articulation and/or occlusion data is provided with the digital version of the dental model, attachment interfaces 716 such as slots, holes, notches, alignment guides, or the like, may automatically added during the modeling step that properly orient the arches 702, 704 in the articulator 712 (provided, of course, the type or dimensions of the articulator are known). The mechanical interface between the articulator 712 and the arches 702, 704 may include screws, interlocking tongue and groove regions, or other mechanical components to removably attach the arches 702, 704 to the articulator. Where a commercial articulator 712 also includes positioning adjustments, the output of the modeling step(s) may also specify one or more settings for these adjustments, which may be included along with a digital dental model, or directly physically marked onto the model for reproduction during fabrication. In another useful technique for aligning the arches 702, 704 one or more outside edges of the upper arch 702 model and the lower arch 704 model may be beveled so that, when placed on a flat surface along that edge, the teeth of the arches 702, 704 remain in their occluded orientation. This may be accomplished by, for example, virtually placing the arches 702, 704 in occlusion within a modeling environment, and then defining a plane within the environment that crosses both arches 702, 704. As illustrated in FIG. 7, a rear edge where the articulator 712 attaches to the model 700 defines such a plane, however one or more additional areas of the edge may be similarly modified, such as the side edges, the front edge, or intermediate regions of the edge of the model 700.

More generally, the fabrication technologies described above may be used in combination with a variety of digital modeling tools to directly fabricate dental objects such as restorations, prosthetics, appliances, and hardware, as well as a variety of interim components of dental manufacture used to create any of the foregoing. A more detailed description of techniques for fabricating articulated dental models is provided below with reference to FIG. 12 et seq.

Figure 8A:
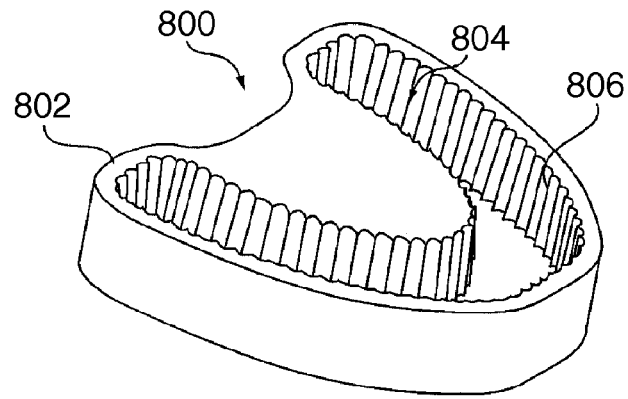
FIGS. 8A-8C show a number of dental objects that can be fabricated from a three-dimensional representation of dentition.
Figure 8B:
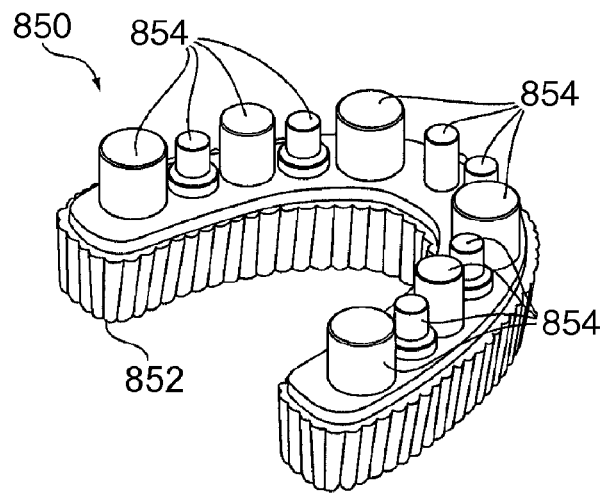
Figure 8C:
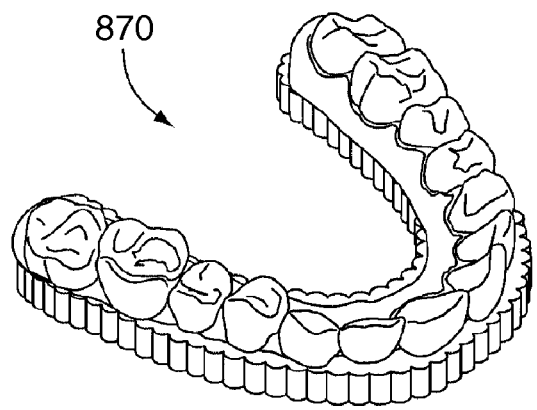

FIG. 8 shows a number of dental objects that can be fabricated from a three-dimensional representation of dentition. In particular, FIG. 8A shows a tray 800 for a dental model and FIG. 8B shows a base 850 for a dental model, and FIG. 8C shows a pre-articulated arch 870 for use with the tray 800 of FIG. 8A.

The tray 800 of FIG. 8A may include a mass 802 with a receptacle 804 such as a groove or indentation and one or more mechanical registration features 806, such as ridges, grooves, slots, or any other physical features that might be used to receive a base (FIG. 8B) into the tray 800 in a predetermined orientation. The mass 802 may be shaped and sized for use with an articulator. In certain embodiments, the mass 802 may be shaped and sized for a particular commercially available articulator. The receptacle 804 and the mechanical registration features 806 may be custom designed for a particular dental model, or they may be standardized so that any base 850 (FIG. 8B) may be modeled with a mating form to the standardized tray 800. In such embodiments, the tray 800 may be mass produced using a process such as injection molding, or any other suitable high volume, low cost manufacturing process. The tray 800 may be mass produced in a number of sizes, such as small, medium, and large, to accommodate various rough sizes of dentition, or the tray 800 may be mass produced in a number of sizes adapted for specific commercially available articulators, or the tray 800 may be mass produced in a single size. Thus, the tray 800 may be created from a three-dimensional digital model of dentition in the modeling step(s) described above, or the tray 800 may be mass produced.

It will be appreciated that, while the physical registration features 806 of the tray 800 may be adapted to receive a base (FIG. 8) for an entire arch of dentition, the physical registration features 806 may also, or instead, be used to orient a single die (not shown), or a number of dies within a dental model such as an articulated dental model. In one embodiment, an entire arch may be precut and preindexed within a virtual environment in the modeling step(s) described above, using varying degrees of automation. Thus, while FIG. 8B shows a unitary base 850 for a dental model, the base 850 may actually consist of one or more precut, preindexed dies, and/or a unitary base for any remaining dentition from a digital model.

The base 850 of FIG. 8B may be created from a three-dimensional digital model of dentition in the modeling step(s) described above. The base 850 may include one or more physical registration features 852 such as ridges, grooves, slots, or any other physical features that might be used to fit the base to the tray into the tray 800 in a predetermined orientation. The base 850 may also include one or more keys 854 for receiving individual teeth or groups of teeth in a dental model. Each key 854 may have a unique shape and or size so that each tooth or group of teeth in the dental model is uniquely indexed to a location on the base 850. While the keys 854 are depicted as cylindrical posts, it will be appreciated that any mechanical registration scheme may be employed to provide a unique location on the base 850 for each tooth or group of teeth in a dental model, including pairs of pins, grooves, slots, varying shapes or impressions, and so forth.

The base 870 of FIG. 8C may be created from a three-dimensional digital model of dentition in the modeling step(s) described above. The base 870 may, in general function resemble the base 850 of FIG. 8B, and may be precut, preindexed, and/or pre-articulated as described herein, except that the base 870 of FIG. 8C includes a surface model of dentition registered to the tray 800, rather than indexed sites for individual teeth of the model as with the base 850 of FIG. 8B.

Although not depicted in FIG. 8, it will be understood that individual teeth or groups of teeth may also be created in a modeling step such that they mate to the keys 854 of the base in a unique arrangement. Varying degrees of automation may be provided for such modeling steps in which, for example, a computerized process fully automates the location of natural teeth and/or surface preparations within the digital model of dentition, or a human identifies some teeth or portions of teeth to assist a computerized process, or a fully manual process in which a human operator places a base 850 and keys within a volumetric representation of dentition. Thus for example, a dental model may be virtually created and directly fabricated that includes a base 850 with holes preprinted for one or more corresponding pins on one or more dies, which may also be directly fabricated from the digital dental model with preprinted, matching pins. In this example, the dental model may be directly printed from the digital model as a plurality of preindexed components ready for assembly at a dental laboratory.

In addition, as noted above, the model may be prearticulated so that the fabricated dental model assembles on an articulator into a model that articulates in a manner corresponding to articulation of the source dentition. This may include various aspects of static articulation such as occlusal contact points and arch positions in various types of occlusion, as well as dynamic occlusion such as (where available from the digital model or supporting data) lateral excursions, jaw motion, and the like.

In one embodiment, the base 850 may be used to orient a dental model within an articulator. Articulated models are used by a dental laboratory technician to determine how to contour the anatomy of a crown or other prosthetic so as to maintain, or in some cases, improve the bite of a patient. By pre-articulating the models during a modeling and fabrication process, a laboratory may save considerable time and effort. In the traditional process, labs are forced to prepare plaster dental arch models from physical impressions taken by a dentist, and manually mount dental arch models into a face bow, a hinged apparatus that simulates the jaw of the patient. The alignment is then manually performed on the mounted models with reference to articulation paper—wax paper on which the patient bites—received from a dentist.

Using information concerning a particular articulator, such as a predetermined commercially available articulator, a particular tray 800, such as a mass-produced tray shaped for use with the articulator, and a three-dimensional representation of dentition that includes articulation and/or occlusion information, the base 850 may readily be adapted to orient teeth within the articulated dental model in their natural occlusion and/or with their natural articulation. In general, this may be achieved by positioning the arches of the digital model in occlusion and locating a hinge or pivot point for an articulator relative to the digital model. The base 850 may then be adapted to bridge any space between a virtual model of the mass-produced tray, as oriented relative to the hinge of the articulator, and the teeth of the digital model of dentition. When the resulting base 850 and any teeth or groups of teeth are fabricated, the articulated model can be assembled using the registration features discussed above to obtain a properly articulated dental model, that is, a model with articulation and/or occlusion corresponding to the source of the digital dental model such as a dental patient.

It will be understood that, while a full arch model is depicted in FIG. 8, the tray 800 and base 850 may be for a quadrant, or one or more teeth of a quadrant, along with one or more opposing teeth, for use in an articulator that does not require a full arch.

Leveraging rapid fabrication technologies such as milling, stereo lithography, and digital light processing allows for the virtual creation and direct fabrication of the individual components of a precut, preindexed, and/or prearticulated dental model. Thus in one embodiment, disclosed herein is a method and system for fabricating a dental model including a plurality of components. While this may include the components of a dental model described above, it may also, or instead, include other components such as investment molds, waxups, and so forth, which may be modeled with varying degrees of automation and transmitted to a dental laboratory or rapid manufacturer as a virtual model of a kit of cooperating dental components. Some or all of the components of the kit may then be directly fabricated from the virtual model, which may be fabricated with an interconnecting wireframe or other structure to maintain components of the kit in a connected relationship until finishing and assembly by a dental technician. Additional examples of these general techniques are provided below.

Figure 9:
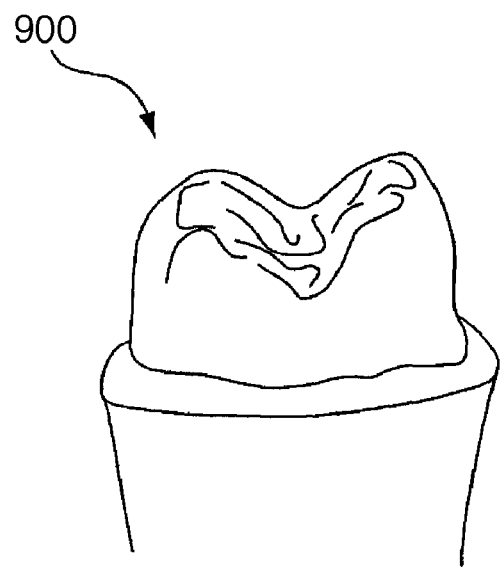
FIG. 9 shows a dental object that can be fabricated from a three-dimensional representation of dentition.

FIG. 9 shows a dental object that can be fabricated from a three-dimensional representation of dentition. More particularly, a waxup 900 of a typical single tooth dental die is shown. Waxups may be employed in a lost wax fabrication process to form restorations or an investment casting chamber or other interim components of dental manufacture. For example, the waxup may instead be employed to create a pressable mold for use with a press-to-zirconium restoration, a press- to alumina restoration, or a pressable ceramic restoration. Waxups may be cosmetic or diagnostic models used first to test a restoration (or other dental object) design, and then to physically fabricate the final restoration in a lost wax process. In a conventional dental fabrication process, a waxup is formed by placing wax directly on a dental model—applied to a surface prepared for a restoration—and hand-crafting a desired restoration. Using the techniques described herein, a waxup may be fabricated directly from a digital three-dimensional representation. For example, the form of the waxup may be inferred through a direct spatial comparison of a scan of dentition before a preparation to a scan of the dentition after a surface has been prepared for a dental object. Where the prosthetic is cosmetic, rather than simply restorative, a tooth may be automatically, semi-automatically, or manually designed, with the waxup inferred from a spatial comparison of the design to the prepared surface. The digital model of the waxup may then be fabricated using any of the techniques described above.

In addition to capturing the correct form for a waxup, a modeling step for a waxup may include the addition of one or more sprues that provide paths into (for investment material) and/or out of (for venting) an investment chamber used with the waxup. Thus, one or more sprues may be added to the waxup and directly fabricated using any of the techniques described herein. While a waxup of a single die is depicted in FIG. 9, it will be appreciated that a number of variations, such as a waxup for a restoration bridging two or more teeth, are also intended to fall within the meaning of the term waxup as used herein.

Figure 10:
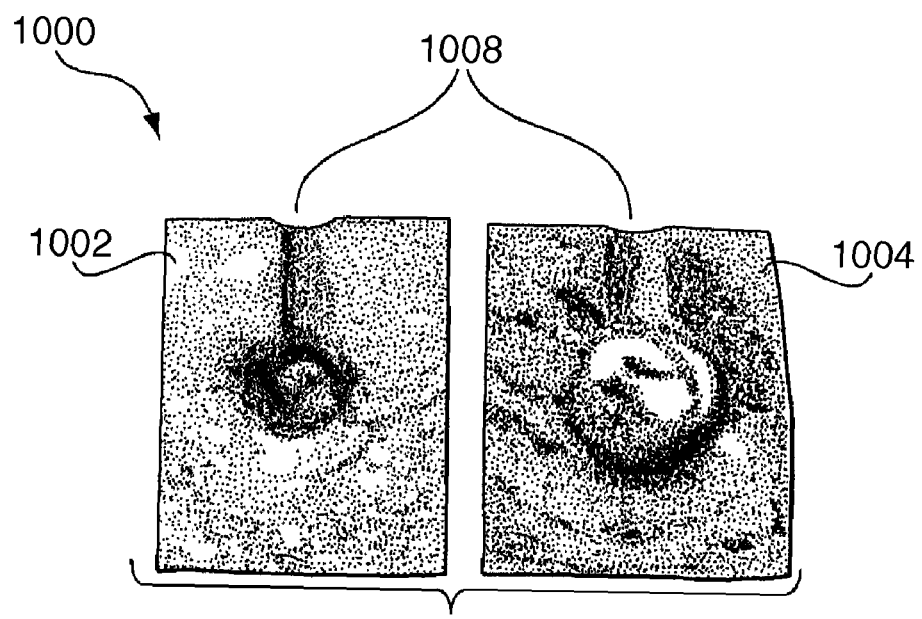
FIG. 10 shows a dental object that can be fabricated from a three-dimensional representation of dentition.

FIG. 10 shows a dental object that can be fabricated from a three-dimensional representation of dentition. More specifically, FIG. 10 illustrates an investment casting chamber 1000 for a single unit pressed or metal restoration. Investment chambers are used in a lost wax process to create metal or ceramic-pressed copings or final restorations. The investment chamber 1000 includes a first mold 1002 and a second mold 1004 which, when placed together, enclose a space defining a restoration geometry. The molds 1002, 1004 may also include a path 1008 for investment. In a conventional dental fabrication procedure, the investment casting chamber 1000 is physically formed from a model such as the waxup described above. However, applying the principles described herein, the investment chamber 1000 may be virtually created from a digital three-dimensional representation of dentition and directly fabricated using the techniques described above. In one embodiment, a computerized milling machine may be employed to fabricate an investment chamber from a suitable material for investment or pressing.

It will be understood that, while the waxups and investment chambers described above may be used to fabricate full restorations such as crowns in their entirety, they may also, or instead, be employed to fabricate a coping or other substructure for use in a Porcelain-Fused-to-Metal ("PFM") restoration, or any other technique in which the final restoration is fabricated in a number of steps that include creation of a substructure.

Thus there is disclosed herein a method of fabricating casting models from three-dimensional surface data captured during an intraoral scan of a dental patient's mouth. While any number of suitable virtual modeling steps may be performed to obtain a digital version of the casting model, the entire process may advantageously be performed without resort to intermediate physical modeling. The casting model may include the investment chamber described above or other investment molds or pressed ceramic molds, as well as an investment cast for an investment mold such as a model of a full restoration, a coping, or a full anatomical form of one or more teeth.

While not depicted in FIG. 10, it will be understood that other molds may be fabricated using the techniques described herein. For example, a bruxism or snoring night guard may be fabricated from a soft plastic or rubber. The guard may be virtually designed during the modeling step(s) described above, and a corresponding mold may be virtually created based upon the digital design for the guard. The mold may then be fabricated from any suitable material using the techniques described herein, and the mold may be filled with a pourable, curable polymer or other substance that will dry or cure into the night guard. Still more generally, any dental object suitable for fabrication in a casting or molding process may advantageously be fabricated using a mold, cast, or other similar device created directly from a digital model of corresponding human dentition.

Figure 11:
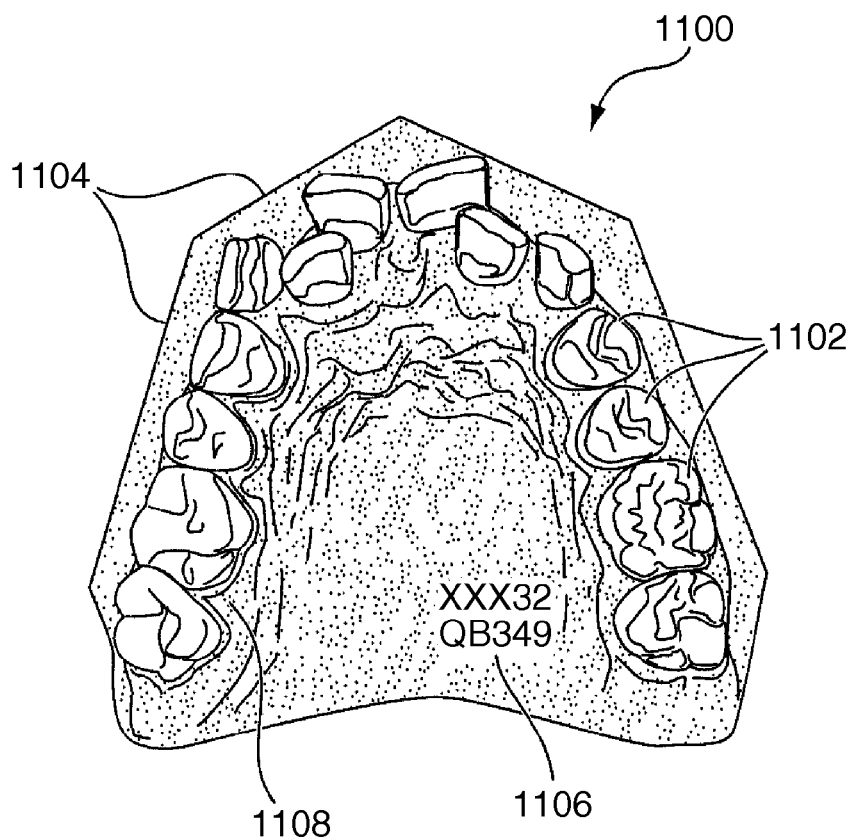
FIG. 11 is a top view of a digital representation of a digital dental model.

FIG. 11 is a top view of a digital representation of a digital dental model. The digital dental model 1100 may include a three-dimensional digital surface representation of a plurality of teeth 1102 in a dental arch, such as used for a dental cast or other dental object. The digital dental model 1100 may also include a number of features added during a modeling step as described above.

For example, the digital dental model 1100 may include one or more beveled edges 1104, as described above in reference to FIG. 7. These edges 1104 may serve to align, e.g., top and bottom arches of a full dental model in an occluded relationship when the two pieces of the model are placed on a flat surface. This feature may aid in handling and working with a physical realization of the full dental model. The edges 1104 may be added to an initial digital representation of scan data from an intraoral scan of dentition, and reproduced in a dental model fabricated from the digital model using any of the techniques described above.

As another example, the digital dental model 1100 may include one or more markings 1106. While depicted as printed text, it will be understood that a variety of markings may be added to the digital dental model 1100 including coloring or text created with pigment, embossment or other three-dimensional surface markings, bar codes, graphics, and so forth. The marking may perform a number of functions such as specifying a physical arrangement of model components or specifying a location of a component within a model, identifying a source or intended destination of the digital dental model 1100, identifying a stock keeping unit ("sku") or other inventory number of a component, or highlighting a region of dental significance. For example, the markings 1106 may identify features such as a restoration margin, a soft tissue boundary, an alignment or occlusion point for a pair of arches, an undercut area for design of a removable prosthetic framework, an orthodontic bracket position or positioning guide, and the like. The markings 1106 include an identification aid concerning the model such as a marking that identifies a patient, a dentist, or a dental laboratory. The marking 1106 may include a logo, such as of a dental laboratory, a bar code, a stock keeping unit code, or any other code that uniquely identifies the model or associates the model with a category of models. The markings 1106 may provide conceptual guides such as a fiducial or a calibration landmark. The markings 1106 may also include a void space to receive, e.g., an RFID tag or other tracking device that may be used to manage an inventory of dental models.

The markings 1106 may, as a specific example, show a margin as a highly contrasted line around a prepared tooth surface. As another example, the prepared surface may itself be marked in a different color from the rest of the model for easy visual identification. These and other markings may be added to a digital dental model 1100, which may be fabricated using any of the techniques described above to provide a marked dental model.

The digital dental model 1100 may also include soft tissue 1108 such as gums, palate, and so forth. In some embodiments, the soft tissue 1108 may be independently modeled and fabricated. This may entail a degree of estimation concerning the shape of teeth below the gumline, which may be supplemented by one or more direct measurements or scans of sub-gumline dentition or models of characteristic tooth shapes. The soft tissue 1108 may be fabricated using any of the techniques described above, and in particular, fabrication techniques that can yield a pliable fabricated model adapted for removal and reattachment to a corresponding model of the hard dentition. The physical soft tissue model may be fabricated from a material that includes a property of live soft tissue such as color, texture, or consistency, or from a material that can be cured to have such properties. The physical soft tissue model may usefully serve to simulate planned soft tissue contour after healing, or to provide a template or surgical guide to aid a clinician during a surgical procedure.

Figure 12:
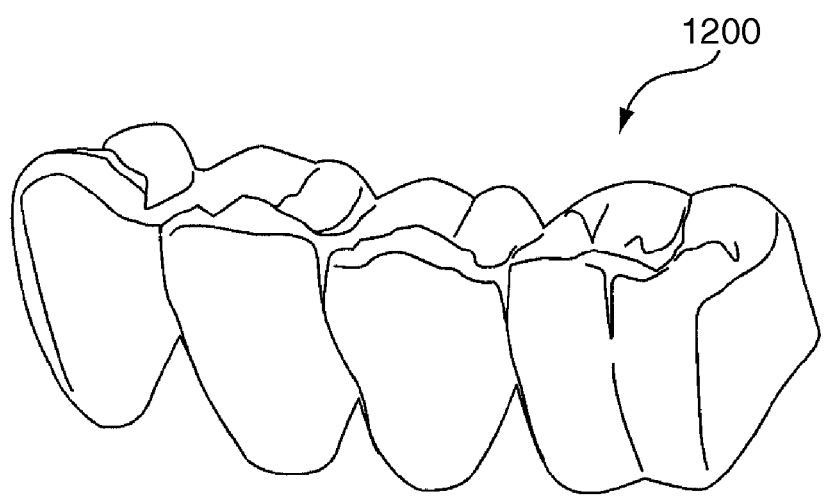
FIG. 12 shows a restoration that can be fabricated from a three-dimensional representation of dentition.

FIG. 12 shows a restoration that can be fabricated from a three-dimensional representation of dentition. It will be understood that, while a multi-tooth bridge is depicted, the restoration 1200 may be any indirect restoration or appliance—as distinguished from direct restorations such as amalgams that are created directly within a dental patient's mouth—suitable for manufacture using the techniques described herein. Thus the restoration 1200 may include an array of components that restore the structure and/or function of existing dentition, such as crowns, bridges, veneers, inlays, onlays, composites, temporary restorations, and various substructures such as copings and the like. Other dental objects such as dentures, partial dentures, implants, retained dentures and so forth may also be directly fabricated from a suitably manipulated model of human dentition and/or any surface preparations of the dentition for the restoration(s).

The modeling step(s) may include inferring a model from a comparison of pre-preparation and post-preparation scans of a restoration site. Where cosmetic or clinically indicated enhancements or other alterations are indicated, the modeling step(s) may also, or instead, included the virtual creation of a target three-dimensional form for one or more teeth according to aesthetic or other dental principles. The creation of a target form may be automated, semi-automated, or manual, although at least some degree of automation is likely to be used for creation of a full three-dimensional structure. In addition, the modeling step(s) may include adapting the target form to any surrounding dentition including opposing and adjacent teeth. A model for the restoration 1200 (or other dental object as described above) may then be inferred from a comparison of surface preparation (if any) obtained from a scan of a dental patient's mouth to the target form for the restoration 1200.

Fabrication may include any of the fabrication techniques described above. For example, the restoration 1200 may be fabricated using computerized milling of a pre-formed ceramic blank, such as a zirconia ceramic having a nanocrystalline porous structure. The resulting product may then be sintered into a hard ceramic structure. Sintering may cause some shrinkage—uniform in all dimensions for suitable starting materials—and the milled product may be modeled with a correspondingly larger size in order for the final product to sinter to suitable dimensions for the restoration site. A veneer may then be applied to achieve a restoration that resembles natural human dentition. As above, the model may be sized to account for a thickness of veneer applied to the milled and sintered product.

As another example, fabrication may include three-dimensional printing or fabricating with a stereo lithography apparatus. The fabrication may be performed with a material that inherently possesses, or cures to possess, or can otherwise be processed to possess one or more characteristics of human dentition, such as color, hardness, strength, wear resistance, texture, and biocompatibility. For example, the material may include a sinterable metal and/or ceramic, or an appropriate resin or other polymer, along with any additives suitable for printing or stereo lithography processes. Suitable materials are known in the three-dimensional printing and stereo lithography arts. In one embodiment, a biocompatible veneer may be applied to the fabricated model.

In one embodiment, a temporary restoration may be three-dimensionally printed into a printed model of any suitable material, and the printed model may be used with a copy milling machine—i.e., a milling machine for transferring a physical form from one material such as the printed model to another material such as a ceramic or other material suitable for a temporary restoration. The digital source for the printed model may, at the same time or any other convenient time for the dentist, be transmitted to a remote facility such as a rapid manufacturer or a dental laboratory for manufacture of a permanent restoration. The temporary restoration may be replaced with the permanent restoration at a subsequent dental visit by a dental patient.

An application of the foregoing techniques and technologies is now described in greater detail with respect to a dental articulator with an alignment grid.

Figure 13:
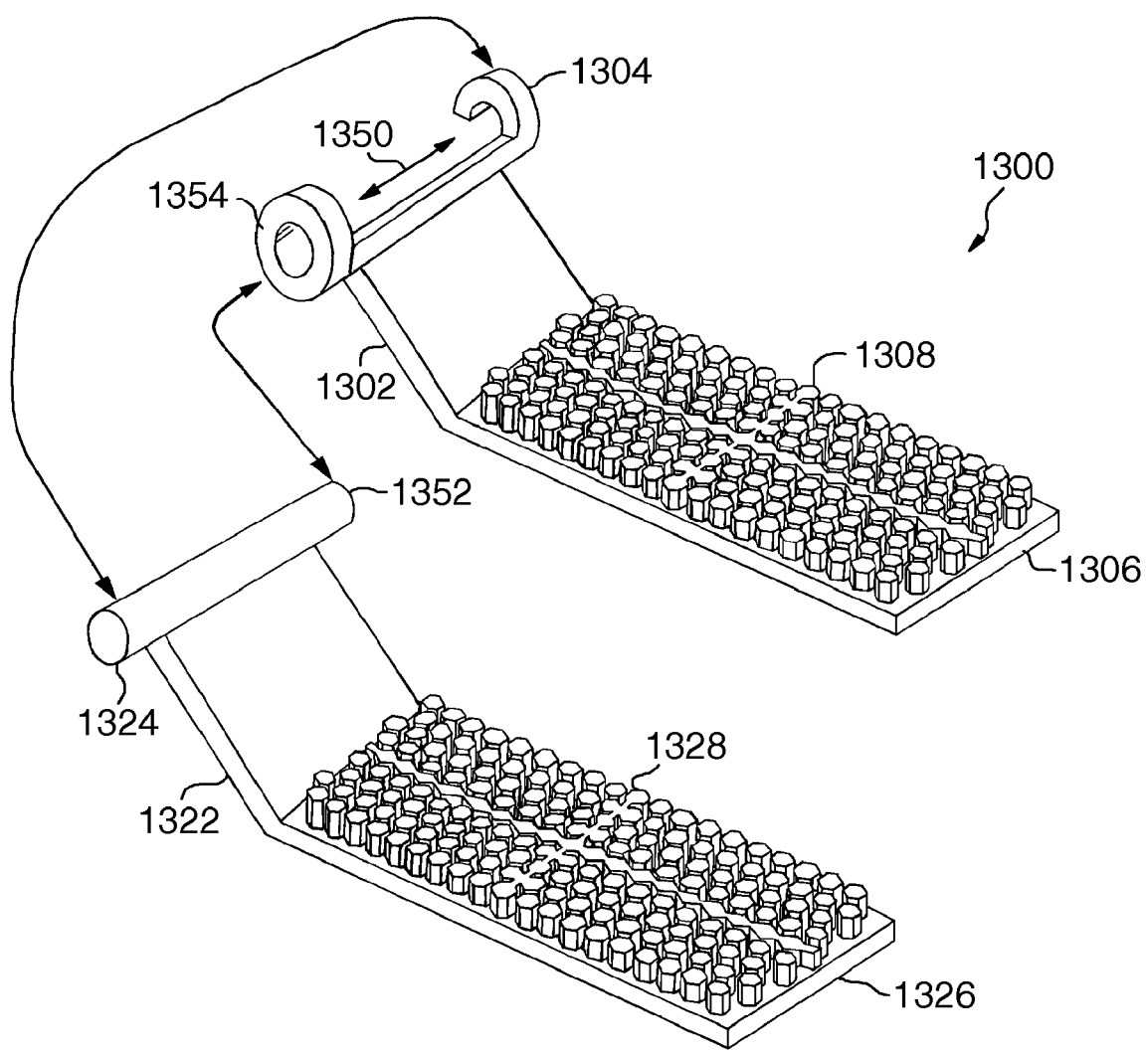
FIG. 13 shows a dental articulator.

FIG. 13 illustrates an articulator 1300 that may be used with objects fabricated from a three-dimensional representation of dentition. The articulator includes a first arm 1302 and a second arm 1322 each having a mounting surface end 1306, 1326 and an opposing pivot end 1304, 1324 respectively. The second arm 1322 and the first arm 1302 may slidably and detachably engage at their respective pivot ends 1304, 1324 through a lateral motion as indicated by an arrow 1350. The arms 1302, 1322 may, once so engaged, pivot on a pin, an axle, bearings, or other structure suitable for rotational engagement of the arms 1302, 1322. In the depicted embodiment, the arms engage and pivot through an interlocking pin 1352 on the second arm 1322 which is received into a circular retainer 1354 on the first arm 1302. Opposite of their pivot end, each arm 1302, 1324 may have a mounting surface 1308, 1328 to receive one or more dental objects that have a corresponding geometry in a predetermined orientation and position.

While a simple rotational engagement is one convenient technique for moveably attaching the arms 1302, 1322 to one another, it will be understood that other techniques may be employed including rotational engagement having a more complex or varied rotational or curvilinear path controlled by a number of interconnected parts, as well as a sliding engagement, such as along posts, that accommodates straight, linear engagement and disengagement of the opposing mounting surfaces 1308, 1328 and any workpieces attached thereto.

The mounting surfaces 1308, 1328 may include a raised surface with a regular geometry or reference grid such as a regular pattern of hexagons, circles, triangles, squares, or the like. A regular geometry with centers spaced at a pitch of, e.g., 2 mm, or in other embodiments, between about 1 mm and 5 mm, or more generally, between 0.5 mm and 10 mm, may provide significant advantages. Unlike the dental objects attached thereto (which are typically specific to a dental patient), the articulator 1300 may be mass produced with very high accuracy. The injection molded parts may be further refined with computerized milling or the like to improve local and global accuracy of the reference grid relative to an electronic model thereof. The resulting mounting surfaces 1308, 1328 may provide accuracy on the order of 25 microns for center placement of a repeating geometry. Thus, each hexagon (or circle, square, etc.) may be accurately centered.

By contrast, the corresponding dental objects (not shown) may be produced using a process with, e.g., pliable materials or an unavoidable degree of, for example, curing or thermal deformation that may affect overall geometry. The use of a highly accurate reference grid for placement of objects that repeats within a small range (e.g., less than 2 mm) ensures localized accuracy for objects attached to the grid. That is, when the corresponding grid is applied to a digital model and a physical object is fabricated from the digital model, dimensional accuracy of the physical object can be confirmed (in at least two dimensions) by mating the object to a known, accurate reference grid. By embedding this reference grid into the articulator 1300, a localized accuracy check is implicitly performed each time an object is attached to the grid. It will be understood that, while a repeating, hexagonal reference grid is depicted in FIG. 13 et seq., any number of variations may be employed including regular and irregular spacing (which may also register each object in a unique location on the grid), and a variety of repeating or non-repeating shapes. Thus, in general, terms such as grid, regular grid, regular geometry, alignment grid, reference grid, and the like will be understood to refer to any geometric pattern that can be imposed on an articulator in a mass production process with sufficient accuracy to ensure localized accuracy of objects mated thereto. Where irregular patterns, such as random patterns or varying shapes, are employed, it will be understood that a relevant characteristic may be feature size rather than center spacing. Thus, individual shapes may be used within a pattern that has relatively large center spacing, relatively small center spacing, or varying center spacing, provided features of the shapes within the reference grid provide features that locally verify accuracy of a corresponding model. The features may include holes, arcs, angles, spurs, or any combination of these, or any other suitable geometric pattern or patterns. The spacing of these features may be any distance suitable for the desired localization of accuracy, such as 2 mm, 3 mm, between about 1 mm and 5 mm, or more generally, between 0.5 mm and 10 mm, and each shape may include one or more features.

In other embodiments, similar alignment grids may be applied along other plane surfaces of fabricated dental objects, provided they do not interfere with the creation of final dental works, such as along sides or other handling surfaces thereof. These may serve as additional dimensional checks even where they are not used for alignment of various pieces in an articulator or the like.

It will also be understood that additional advantages may accrue from such an alignment grid. By using a significant number of mating surfaces, a good tension or friction fit may be maintained between the articulator 1300 and pieces attached thereto. This may simplify handling of workpieces by mitigating or removing the need for additional fasteners and the like. Further, by distributing this fit along the entire mating surface, or a significant portion thereof, lateral stability of the inserted pieces may be increased for improved handling of the assembled model. Further, the articulator 1300 may be fabricated in a material such as polyphenylsulfone ("PPSF") that provides sufficient hardness and thermal resistance to be washed and reused numerous times.

Figure 14:
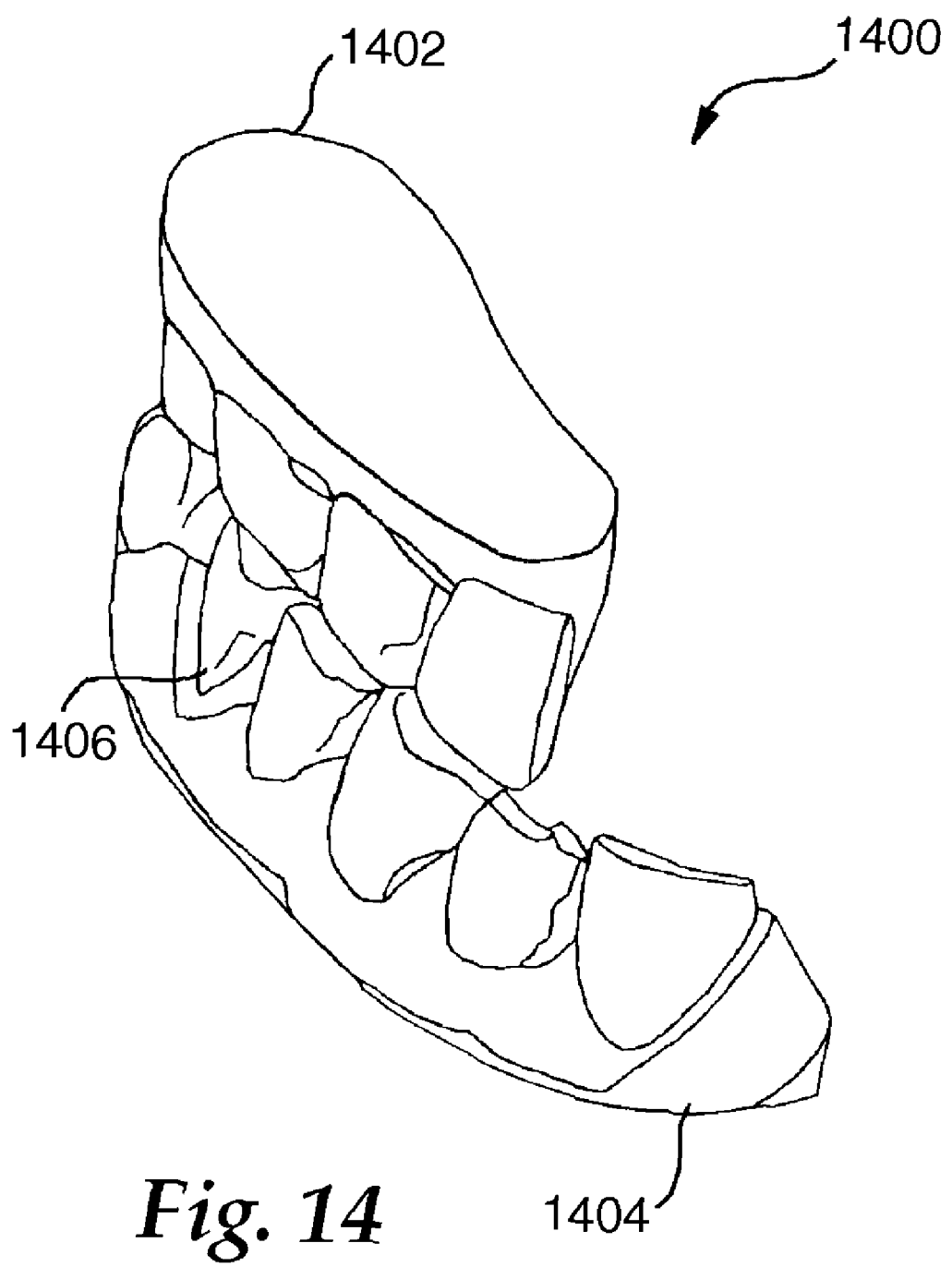
FIG. 14 shows a digital dental model with two partial arches in occlusion.

FIG. 14 shows a digital dental model with two partial arches in occlusion. The model 1400 may include two opposing surfaces such as a partial upper arch 1402 and a partial lower arch 1404 with at least one tooth surface 1404 prepared for an artificial dental object. It will be understood that the depiction of FIG. 14 is an example only. While the figure depicts a partial upper and lower arch with a single tooth prepared for a crown, the digital dental model may include more or less of each opposing arch, and may include a tooth surface prepared for any one or more dental objects suitable for fabrication using the techniques described herein. The opposing surfaces 1402, 1404 may be virtually aligned using, for example digital bite registration, such as by registering the digital objects to a surface scan that spans both arches while the arches are in occlusion, as generally described above.

It will be understood that, while a partial arch model including a prepared tooth surface is depicted in this and the following figures, the techniques described herein may also, or instead, be suitably applied to models with or without prepared tooth surfaces, single tooth models, quads, partial arches, full arches, and so forth.

Figure 15:
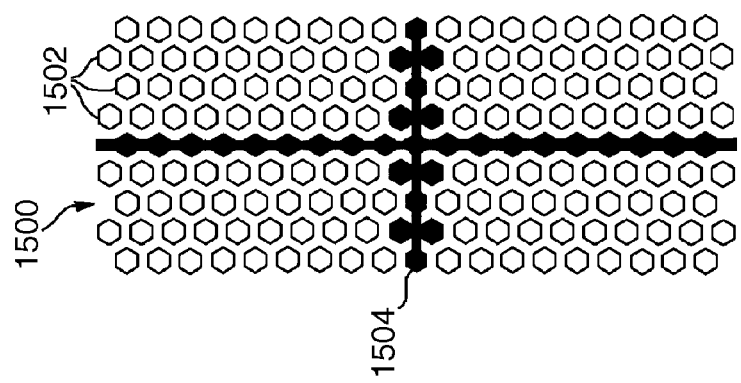
FIG. 15 depicts a cross section of an alignment geometry including a positioning key.

FIG. 15 depicts a cross section of an alignment geometry including a regular geometry and a positioning key. As discussed above, the alignment geometry may include a regular geometry 1500 of hexagons 1502 or other shapes, along with a positioning key 1504 or other mechanical registration feature adapted for unique positioning of one or more dental objects in a plane. In general, the positioning key 1504 mechanically encodes positional information and the regular geometry 1500 enforces local accuracy against a fixed reference array as described above. The regular geometry 1500 and/or positioning key 1504 may be embedded in raised and/or recessed surfaces of mating components such as dental articulators (or bases, and so forth) and components of dental models to capture relative position and orientation of the components.

It will be understood that, while the positioning key 1504 is depicted as an orthogonal line pair, and such a key may be usefully employed with the systems and methods described herein, a variety of other keys and registration schemes may be usefully employed to uniquely position objects in an x-y plane of a mounting surface. Any such technique that would be apparent to one of skill in the art may be employed with the systems described herein, provide it offers suitable scale and detail for the dental models described herein.

When constructing an articulator such as the articulator 1300 described above for use with objects containing the alignment geometry, a number of features may be included to improve ease of use and assembly. For example, the surface on the articulator corresponding to the positioning key 1504 may be raised slightly (e.g., 0.1 mm, 0.5 mm, 1 mm, 2 mm, or any distance between these distances, or any other distance) to provide tactile feedback during assembly. As another example, a single circular element may extend substantially above the surface of the articulator (or above the mating surface of the dental object) as an alignment post, with a corresponding hole in the mating surface. This permits convenient centering of an object by a user during assembly with both visual and tactile feedback. Once centered on the alignment post, further assembly requires only rotational alignment to the alignment geometry and any associated positioning keys. As another example, the opposing surfaces of the articulator and dental object(s) may be provided with a three-dimensional contour (such as a rectangular pyramid) that urges the opposing pieces into alignment during assembly. That is by providing a cone or pyramid shape on one side, and an inverted duplicate of same on the other, the two pieces will tend to move into alignment as they are pressed together, providing gross tactile feedback on proper alignment.

Figure 16:
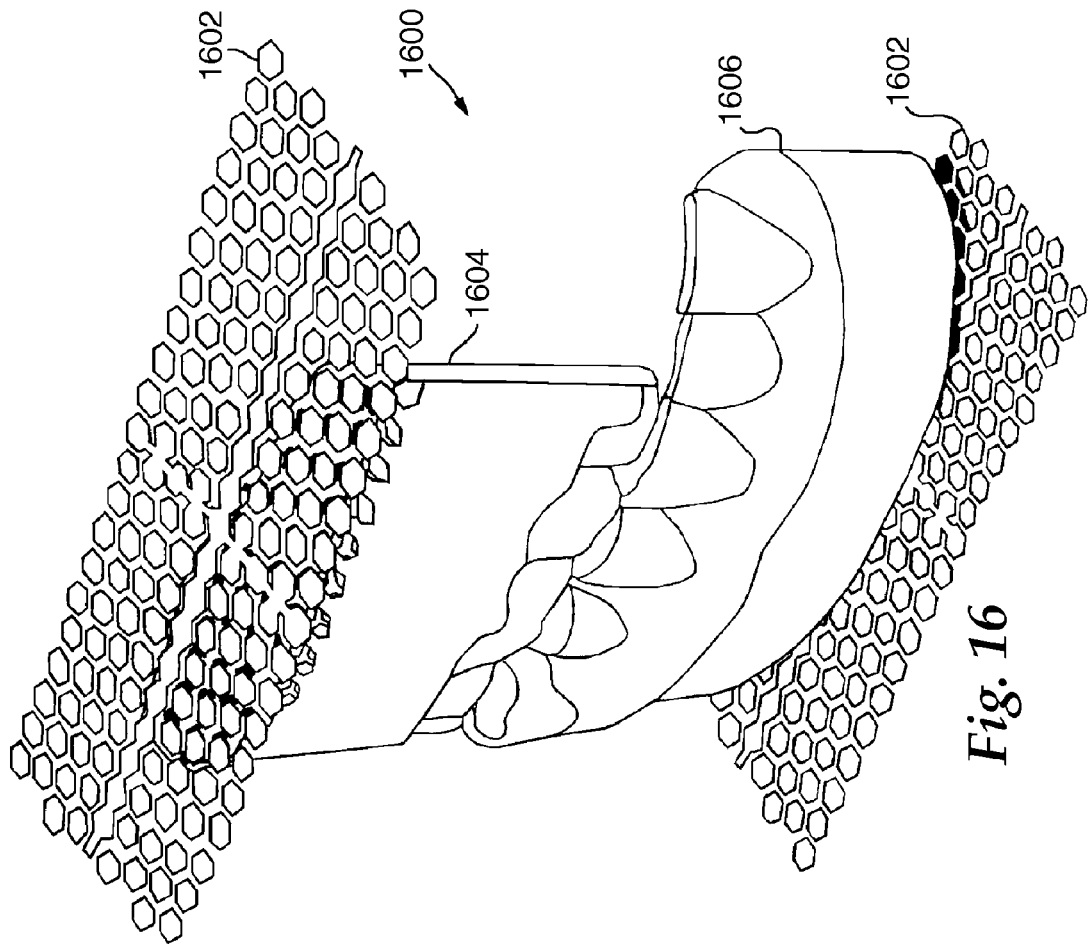
FIG. 16 shows a virtual application of an articulator geometry to a dental model.

FIG. 16 shows a virtual application of an articulator geometry to a dental model. In this digital model 1600, an alignment geometry 1602 such as any of the alignment geometries described above, may be positioned in two separated, parallel planes corresponding to the operative positions of two halves of a dental articulator having the same geometry. A dental model, which may include an upper surface 1604 and a lower surface 1606 in occlusion as described generally above, may be positioned within the planes of the alignment geometry 1602, either manually or automatically (e.g., by alignment relative to top and bottom planes of the dental model).

The dental model may then be extended (again, either automatically or manually) to intersect the planes of the alignment geometry 1602. A three-dimensional model of the alignment geometry 1602 may then be added to the digital model that mechanically corresponds to the alignment geometry of an articulator, such as any of the articulators described above. Where the planes of the alignment geometry 1602 represent innermost bounds of the articulator surfaces, the dental model may then be further extended or extruded to a length corresponding to an outermost bound of the articulator. Where the planes of the alignment geometry 1602 represent outermost bounds of the articulator surfaces, the alignment geometry may be projected inward on the surfaces of the dental model (using, e.g., an exclusive or ("XOR") or other operation) to a depth reaching to the innermost bounds of the articulator surfaces. The resulting digital model 1600 is prefit and prealigned to a dental articulator having corresponding alignment geometry and positioning keys.

It will be understood that, while the articulator described above employs two plane surfaces that are parallel when arches of the model are occluded, this is not strictly required, and any alignment or positioning may be employed that suitably presents occlusion and alignment data to a technician who is fabricating a dental object therefrom. It will also be understood that additional process may be required as will be readily appreciated by one of ordinary skill in the art. For example, the side walls of a PPSF injection molded part may require a pitch of 1° to insure that the part can be removed from a mold. A corresponding pitch may be added to the three-dimensional alignment geometry of the digital model 1600 for a good fit. In addition, tolerances may be varied to increase or decrease the tightness of fit between assembled parts, which may be specified on a part by part, customer by customer, or global basis. In another aspect, the shape of the mating three-dimensional surface of the model need not correspond to the shape of the dental model. That is, the mating surface of the dental model may be digitally fashioned as a base plate larger than the cross-section of the dental object, or as a regular geometry small than the dental model, such as a square or rectangle fit within the cross-sectional bounds of the dental model, or some other shape independent of the cross-sectional shape of the dental model. All such variations are intended to fall within the scope of this disclosure.

Figure 17:
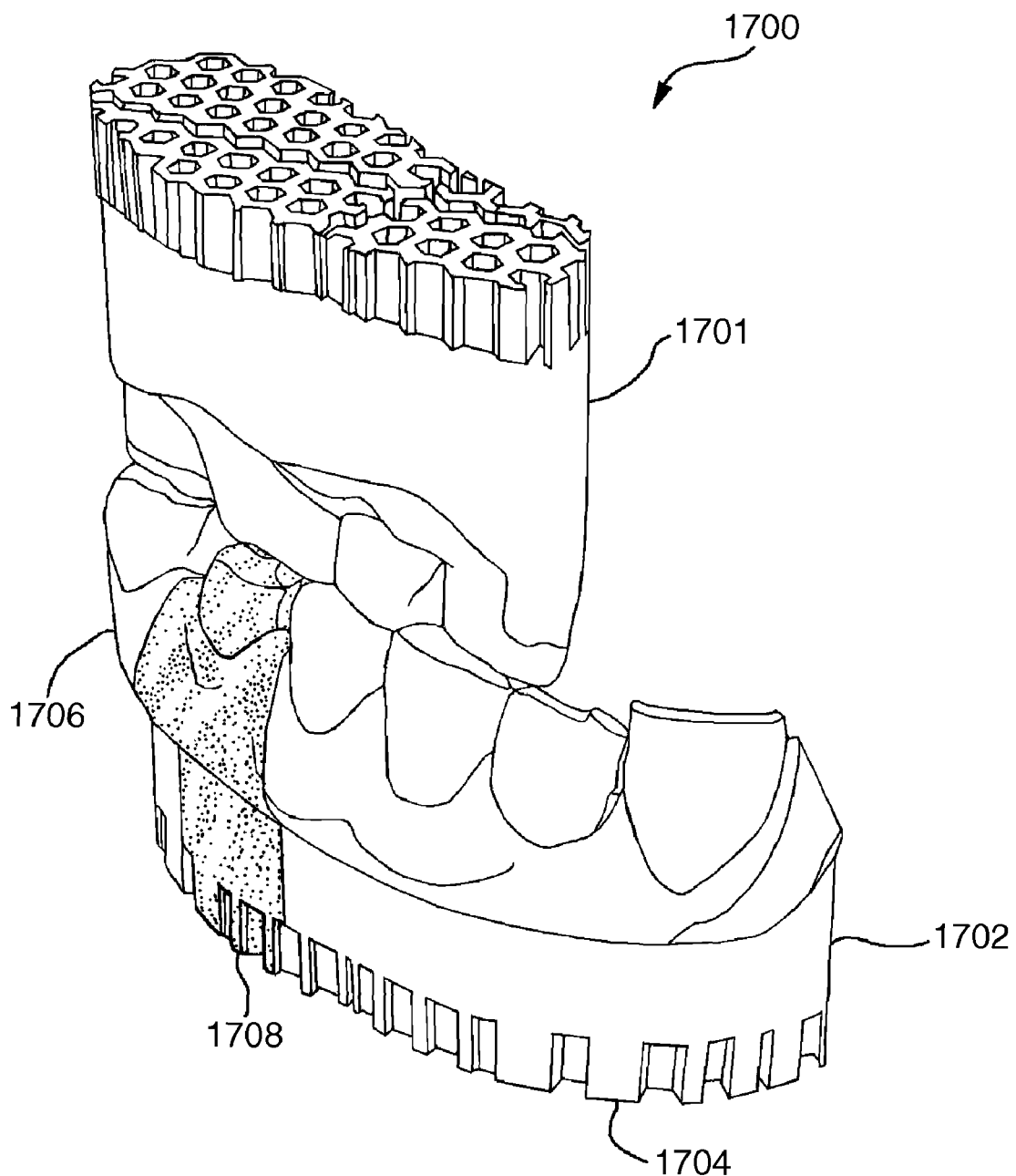
FIG. 17 shows a dental model including alignment geometry.

FIG. 17 shows a dental model including alignment geometry. An upper arch 1701 and a lower arch 1702 generally present features such as a regular geometric array and positioning keys that will mechanically register a physical model fabricated therefrom in correct orientation within a dental articulator such as the articulator 1300 described above. It will be noted that the digital dental model 1700 may be further processed prior to fabrication as described generally above. For example, in conventional dentistry, dies are manually cut from a dental model by a dental technician for preparation of a restoration. However, applying the principles described herein, a die 1708 may be virtually cut from a first and second adjacent regions 1704, 1706 of the lower arch 1702 during a modeling step (as described generally above). Each portion of the model may be separately manufactured, which permits, for example manufacture of the die 1708 from a different material and/or using a different process, as described for example with reference to FIG. 9 above. Thus the die 1708 may be milled from a ceramic while the other regions 1704, 1706 may be fabricated using DLP, stereo-lithography, or three-dimensional printing. For computerized milling or the like, a billet may be preformed with the regular geometry and/or positioning key integrated therein. This may provide an additional advantage of orienting the workpiece in the milling environment, such as through use of a support device with a surface corresponding to the surface(s) of an articulator. Thus in one embodiment, a technique for fabricating pre-cut dental models directly from a digital model is disclosed.

Other modeling techniques described above may also be employed to assist in transitioning from a digital dental model to a physical dental model, such as the virtual die spacing, occlusal relief, ditching of the die, and so forth.

Figure 18:
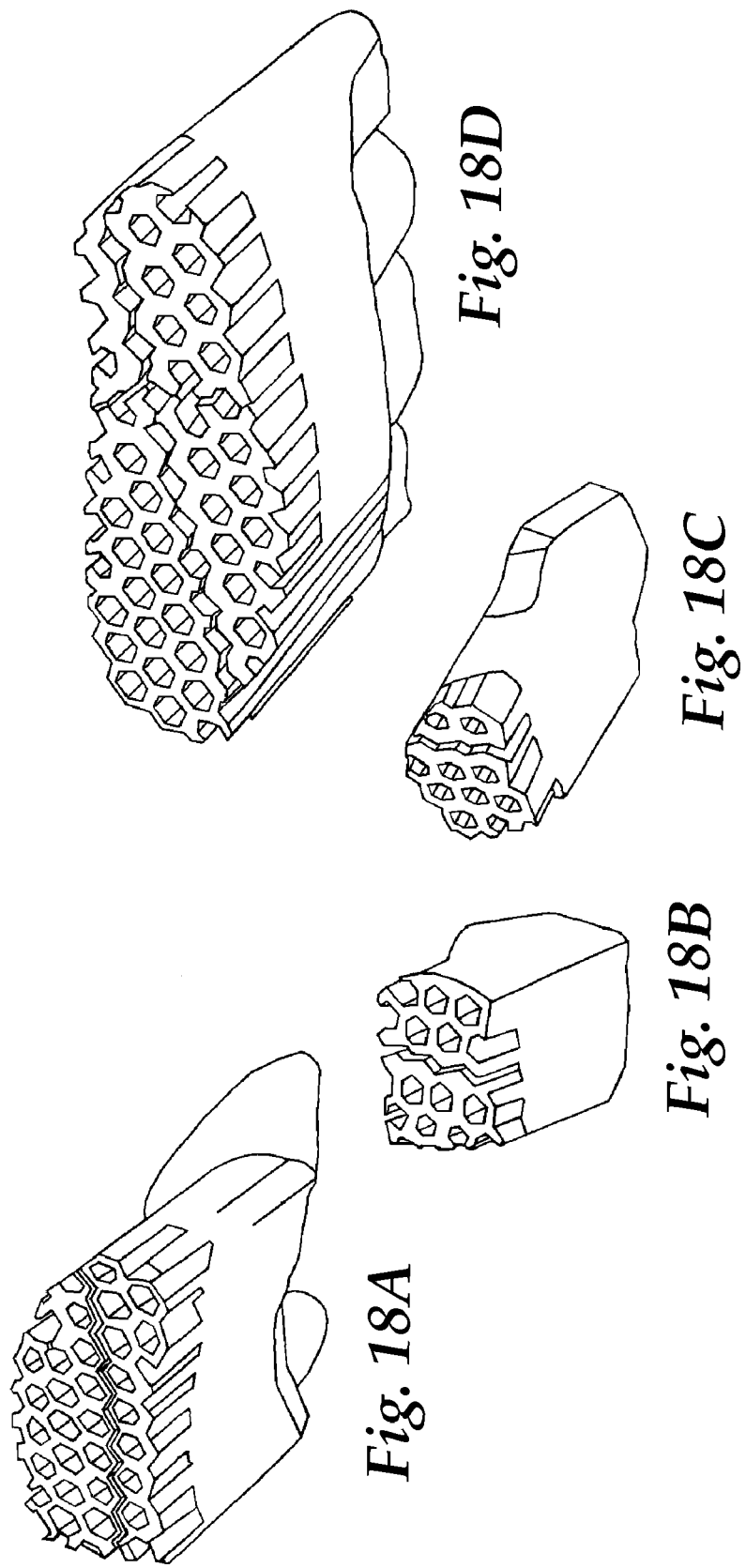
FIG. 18 shows pieces of a dental model fabricated from a digital dental model.

FIG. 18 shows pieces of a dental model fabricated from a digital dental model. FIG. 18A shows a first portion of a lower arch corresponding to a first adjacent region 1706 of a lower arch 1702 in FIG. 17 above. FIG. 18B shows a cut die corresponding to the die 1708 of FIG. 17 above. FIG. 18C shows a second portion of a lower arch corresponding to the second adjacent region 1704 of FIG. 17 above. FIG. 18D shows an upper arch corresponding to the upper arch 1701 of FIG. 17 above.

It will be understood that the pieces of a dental model illustrated in FIGS. 18A-18D may be fabricated in a number of ways. For example they may be fabricated as a kit using, e.g., stereo-lithography or digital light processing as described above, and may include an interconnecting wire frame or other structure to keep the pieces joined together until they reach a dental technician or other handler. They may be fabricated from different materials or using different processes as described generally above. They may include bar codes, embedded radio-frequency identification ("RFID") tags, color coding, or other markings or identification technologies to assist in tracking and handling large numbers of parts.

Figure 19:
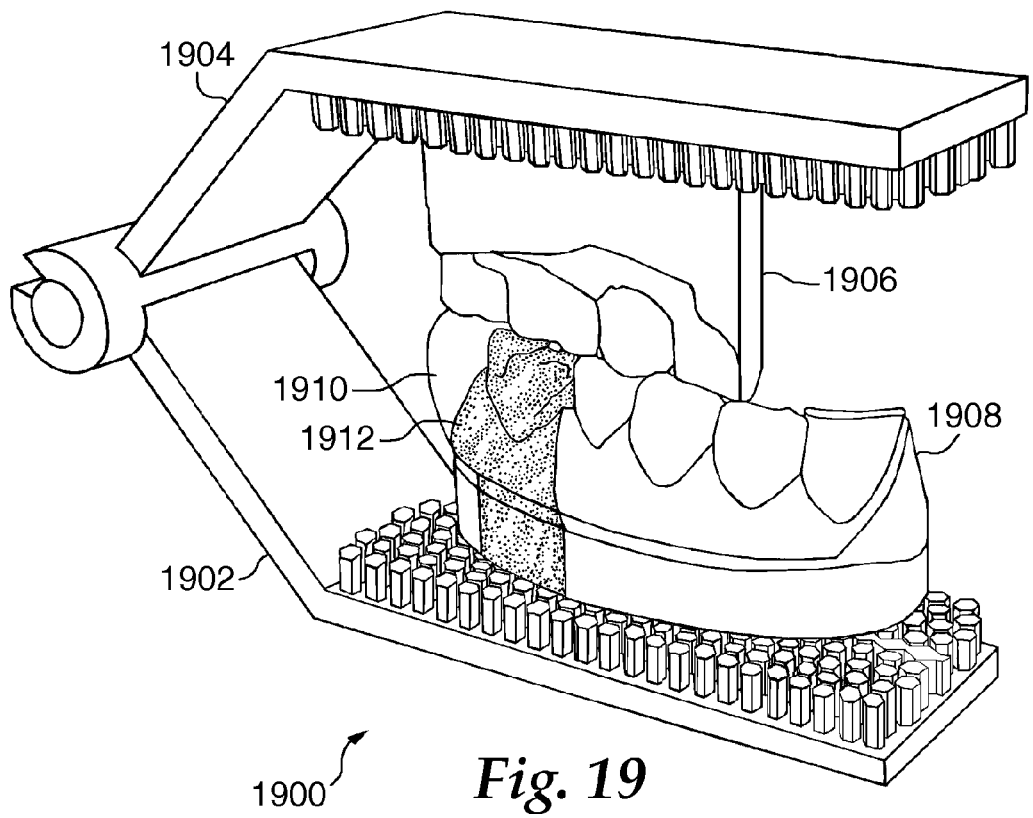
FIG. 19 shows a dental model assembled on an articulator.

FIG. 19 shows a dental model assembled on an articulator. In general, the assembled model may include a first section 1902 and a second section 1904 of an articulator, a first arch 1906 (or partial arch), and a second arch precut into a first piece 1908, a second piece 1910, and a third piece 1912 for use in fabrication of an artificial dental object such as a crown, prosthesis, and the like. A regular geometric array and/or positioning keys molded into the sections 1902, 1904 of the articulator may physically mate with corresponding surfaces of the model pieces 1906, 1908, 1910, 1912 to providing an articulating model that reproduces the orientation of dental structures from a dental patient. The assembled model may capture various aspects of static articulation such as occlusal contact points and arch positions in various types of occlusion, as well as dynamic occlusion such as lateral excursions, jaw motion, and the like.

It will be appreciated that, the mechanical registration features 802 may also, or instead, be used to orient a single die (not shown), or a number of dies within a dental model. In one embodiment, an entire arch may be precut and pre-indexed within a virtual environment in the modeling step(s) described above, using varying degrees of automation.

Figure 20:
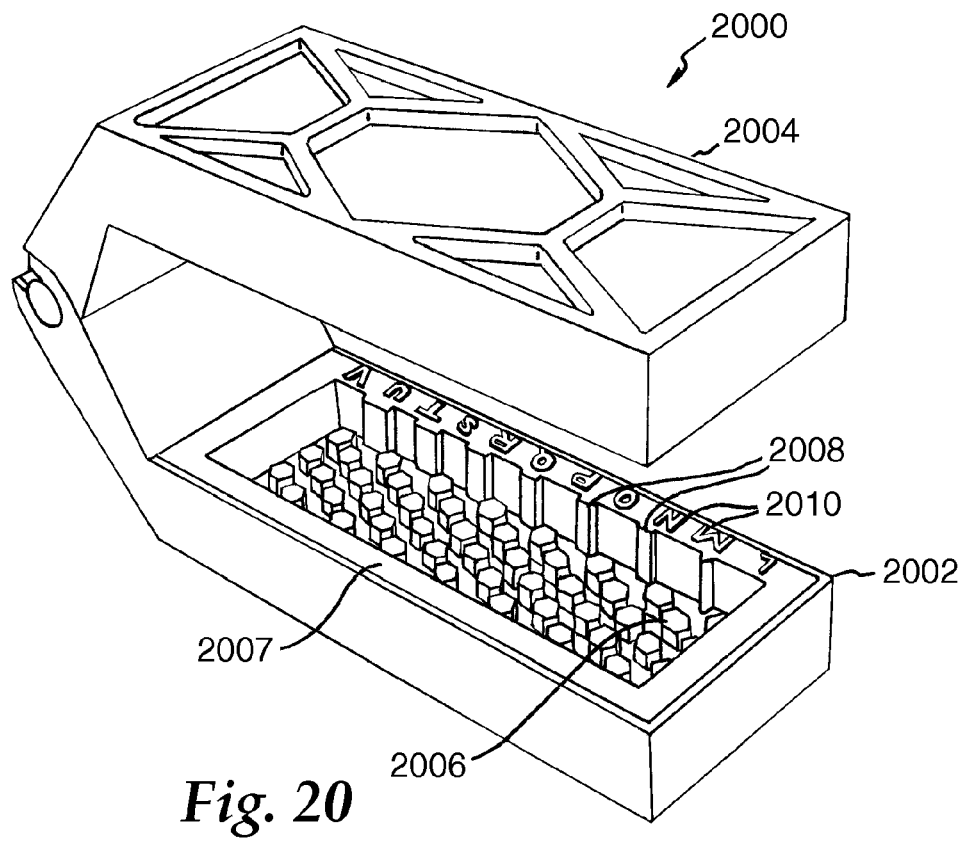
FIG. 20 shows a dental articulator.

FIG. 20 shows another embodiment of a dental articulator. The articulator 2000 may include a first arm 2002 and a second arm 2004, such as the arms described above. Each arm 2002, 2004 may include a mounting surface 2006 with a reference grid surrounded by a retaining wall 2007 that includes a positioning key comprised of a number of alignment guides 2008. Each arm 2002, 2004 may also include visual markings 2010 such as letters or other markings to assist a user in assembling components of a model on the arms 2002, 2004. It will be understood that while visual markings 2010, the retaining wall 2007, the alignment guides 2008, and the regular geometry of the mounting surface 2006 are illustrated only for the first arm 2002, that some or all of these features may also, or instead, be on the opposing second arm 2004 even though they are not visible in the perspective drawing of FIG. 20.

The retaining wall 2007 may provide lateral stability to object inserted into the articulator 2000, or may enhance stability provided by the reference grid as described above. The alignment guides 2008 may provide a positioning key to support unique positioning of separate components within a dental (or other) model. Thus, for example, as depicted in FIG. 20, the alignment guides 2008 may have a gradually increasing width from guide to guide along the retaining wall 2007 in order to provide mechanical registration for a number of pieces. Similarly, variations in spacing, shape, and size may be employed to mechanically register model components within the space defined by the retaining wall 2007. In addition to this mechanical registration, the visual markings 2010, which may be letters, numbers, symbols, or the like, may provide visual indicators of object positioning that are correlated to similar or identical visual markings printed on model components. In this manner, a user assembling objects to the articulator 2000 is provided with visual indicators of position, reinforced with mechanical registration of the alignment guides 2008.

It will also be appreciated that the embodiments described above are by way of example and not limitation. Dental models fabricating using the techniques described herein may include, without limitation, a pre-manufactured base upon which dental models are aligned. More generally, the fabrication technologies described above may be used in combination with a variety of digital modeling tools to directly fabricate dental objects such as restorations, prosthetics, appliances, and hardware, as well as a variety of interim components of dental manufacture used to create any of the foregoing. The dental model, or portions thereof, may be directly printed from the digital model as a plurality of pre-indexed components ready for assembly at a dental laboratory.

Leveraging rapid fabrication technologies such as milling and stereo lithography allows for the virtual creation and direct fabrication of the individual components of a precut, preindexed, and/or prearticulated dental model such as described above with reference to FIGS. 13-20. Thus in one embodiment, disclosed herein is a method and system for fabricating a dental model including a plurality of components. While this may include the components of a dental model described above, it may also, or instead, include other components such as investment molds, waxups, and so forth, which may be modeled with varying degrees of automation and transmitted to a dental laboratory or rapid manufacturer as a virtual model of a kit of cooperating dental components. Some or all of the components of the kit may then be directly fabricated from the virtual model.

Thus there is disclosed herein direct fabrication of restorations and appliances from digital models such as digital surface representations acquired from human dentition. This fabrication, and any of the other fabrication processes described herein may be performed, for example, at a dental laboratory or at an in-office dental laboratory at a dentist's office.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. A device comprising;
   a dental articulator fabricated using a high accuracy injection molding process, the dental articulator including a surface with a fixed reference array; and
   a multi-part dental model including a number of components fabricated with a rapid fabrication facility from a digital model that includes a corresponding fixed reference array to the fixed reference array of the dental articulator, wherein the corresponding fixed reference array spans two or more of the number of components and wherein the rapid fabrication facility has a substantially lower accuracy than the high accuracy injection molding process, each one of the number of components including a positioning key structurally separate from the corresponding fixed reference array that mechanically encodes positional information for the component in the dental articulator and provides gross tactile feedback on a proper positioning and alignment in the dental articulator, wherein the corresponding fixed reference array includes a reference grid formed of a repeating geometry that enforces local accuracy of each one of the number of components against the fixed reference array in the dental articulator without uniquely positioning the dental model in the dental articulator.

2. The device of claim 1 wherein the multi-part dental model includes a dental die.

3. The device of claim 1 wherein the reference grid is a regular geometry having centers spaced at less than 3 mm.

4. The device of claim 1 wherein the reference grid has features spaced at between 0.5 mm and 5 mm.

5. The device of claim 1 further comprising a radio frequency identification tag embedded in at least one of the number of components.

6. The device of claim 1 further comprising a visual identification marking on at least one of the number of components including one or more of text, a bar code, a logo, and a sku.

7. The device of claim 1 wherein the multi-part dental model includes a full arch or a partial arch.

8. The device of claim 1 wherein the positioning key includes an orthogonal line pair.

9. The device of claim 1 wherein the positioning key includes an alignment post.

10. The device of claim 1 wherein the positioning key includes a number of alignment guides.

11. The device of claim 1 wherein the positioning key includes visual markings.

12. The device of claim 1 further comprising one or more visual markings on at least one of the number of components corresponding to one or more corresponding visual markings on the dental articulator, wherein the one or more visual markings on the device and the one or more corresponding visual markings on the dental articulator provide a visual guide to an alignment of the device to the dental articulator.

13. The device of claim 1 wherein the rapid fabrication facility uses one or more of computerized milling, stereolithography, digital light processing, three dimensional printing, selective laser sintering, fused deposition modeling, and laminated object manufacturing.

* * * * *